United States Patent
Giuliano et al.

(10) Patent No.: US 8,609,162 B2
(45) Date of Patent: *Dec. 17, 2013

(54) INTEGRATED NEUROMODULATION SYSTEM FOR MOOD ENHANCEMENT OF A LIVING HUMAN SUBJECT

(71) Applicant: InVivo Beverages LLC, Winter Springs, FL (US)

(72) Inventors: Vincent Giuliano, Winter Springs, FL (US); James Manley, Winter Park, FL (US)

(73) Assignee: InVivo Beverages LLC, Winter Springs, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/689,980

(22) Filed: Nov. 30, 2012

(65) Prior Publication Data

US 2013/0156872 A1     Jun. 20, 2013

Related U.S. Application Data

(60) Provisional application No. 61/709,501, filed on Oct. 4, 2012.

(51) Int. Cl.
A61K 36/48        (2006.01)

(52) U.S. Cl.
USPC .............................. 424/757; 514/46

(58) Field of Classification Search
None
See application file for complete search history.

(56) References Cited

U.S. PATENT DOCUMENTS

| | | | |
|---|---|---|---|
| 6,132,724 A | 10/2000 | Blum | |
| 7,674,482 B2 | 3/2010 | Shell et al. | |
| 7,989,007 B2* | 8/2011 | Giuliano et al. | 424/725 |
| 2009/0214680 A1* | 8/2009 | Giuliano et al. | 424/728 |
| 2011/0064712 A1* | 3/2011 | Amato | 424/94.2 |
| 2012/0177732 A1 | 7/2012 | Buckley | |

FOREIGN PATENT DOCUMENTS

WO         9908681 A1     2/1999

OTHER PUBLICATIONS

Ballenger JC., Benzodiazepine receptors agonists and antagonists, In Sadock VA, Sadock BJ, Kaplan HI (eds.), Kaplan & Sadock's Comprehensive Textbook of Psychiatry (7th ed.), Lippincott Williams & Wilkins, 2000, pp. 2317-2323.
Barker MJ et al., "Cognitive effects of long-term benzodiazepine use: a meta-analysis," CNS Drugs, 2004, 18: 37-48.
Bemben MG et al., "Creatine supplementation and exercise performance; recent findings," Sports Medicine, 2005, 35;107-25.
Brain Lightning, CEREBREX: Nootropics Specification Document; Retrieved Oct. 16, 2012, 13 pages. Available at: http://www.brainlightning.com/.
Clayton AH, "Antidepressant-associated sexual dysfunction: a potentially avoidable therapeutic challenge," Primary Psychiatry 2003, 10: 55-61.
Daly JW et al., "Caffeine-an atypical drug of dependence," Drug Alcohol Depend, 1998, 51: 199-206.
Eilander et al., "Multiple micronutrient supplementation for improving cognitive performance in children: systematic review of randomized controlled trials," Am J Clin: Nutr, Jan. 2010, 91:115-130.
Elia J et al., "Treatment of attention-deficit-hyperactivity disorder," N Engl J Med, 1999, 340;780-788.
Epiphany D1 , Neurotransmitter Support, CerebralHealth,com, Retrieved Jun. 18, 2013, 2 pages. Available at: http://www.cerebralhealth.com/nootropics.php.
Fava M., "Weight gain and anti-depressants," J Clin Psychiatry, 2000, 61(11): 37-41.
Ginzburg R, "Skeletal muscle relaxants," Pharmacotherapy, 2008, 28:207-13.
Hu XH et al., "incidence and duration of side effects and those rated as bothersome with selective serotonin reuptake inhibitor treatment for depression: patient report versus physician estimate," J Clin Psychiatry, 2004, 65: 959-965.
Jay R Hoffman et al., "Examination of a pre-exercise, high energy supplement on exercise performance" Journal of the International Society of Sports Nutrition 2009, 6:2, Published: Jan. 6, 2009, 8 pages.
Kanaly KA et al., "Sexual side effects of SSRI medications: potential treatment strategies for SSRI-induced female sexual dysfunction," Current Women's Health Reports, 2002, 2: 409-416.
Kreider RB et al., "Effects of creatine supplementation on performance and training adaptations," Molecular and Cellular Biochemistry, 2003, 244:89-94.
Marley E et al., "Interactions of monoamine oxidase inhibitors, amines, and foodstuffs," Adv Pharmacol Chemother, 1970, 8:185-239.
Nelson, T et al., "Effects of alcohol intoxication on metamemory and on retrieval from long-term memory," J Experimental Psychology, 1986, 115; 247-254.
Neurotine , Amino Acid Brain Fuel for Healthy Neurons and Synapses, CerebralHealth.com, Retrieved Jun. 18, 2013, 2 pages. Available at: http://www.cerebralhealth.com/nootropics.php.

(Continued)

*Primary Examiner* — Gregory S Emch
(74) *Attorney, Agent, or Firm* — Robert Plotkin, P.C.

(57) ABSTRACT

The present invention is an ingestable blended formulation which will cause a series of distinct biochemical changes in-vivo; initiate desirable psychological consequences in that person; and induce an observable increase in cognitive functions for that living human subject. In particular, the initiated psychological events will generate a positive change in one's personal perceptions, evoke optimism as the subjective state of mind, and elicit a more sociable attitude and favorable mood as the observable behavior of the affected human person. Moreover, in addition to the initiation of a more positive state of mind, another major result and effect of ingesting the blended formulation is an observable amplification of human brain functions and a substantive increase of human concentration, focus and memory.

16 Claims, 1 Drawing Sheet

(56) References Cited

OTHER PUBLICATIONS

Nybo L et al., "Impact of carbohydrate supplementation during endurance training on glycogen storage and performance," Acta Physiol, 2009,197:117-127.

Olfson M et al., "Antidepressant drug therapy and suicide in severely depressed children and adults: a case-control study," Archives of General Psychiatry, 2006, 63: 865-872.

Ratamess NA et al., "Effects of an amino acid/creatine energy supplement on the acute hormonal response to resistance exercise," Int J Sport Nutr Exerc Metab, 2007, 17:608-623.

Rubinow DR, "Treatment strategies after SSRI failure" good news and bad news, N Engl J Med, 2006, 354:1305-1307.

Schuckit, MA, "Depressants," In: Drug and Alcohol Abuse—A Clinical Guide to Diagnosis and Treatment, Chapter 2, Springer, 2006, pp. 41-67.

Shopsin B et al., "Monoamine oxidase inhibitors: potential for drug abuse," Biol Psychiatry, 1976, 11:451-456.

Stewart SA., "The effects of benzodiazepines on cognition," J Clin Psychiatry, 2005, 66: 9-13.

Taylor SL, "Histamine Food Poisoning: Toxicology and Clinical Aspects," Crit Rev Toxicol. 1986;17(2):91-128.

Tunnicliffe JM et al., "Consumption of dietary caffeine and coffee in physically active populations: physiological interactions," Appl Physiol Nutr Metab, 2008, 33:1301-1310.

Turner EH at al., "Selective publication of antidepressant trials and its influence on apparent efficacy." N. Engl J Med, 2008, 358: 252-260.

\* cited by examiner

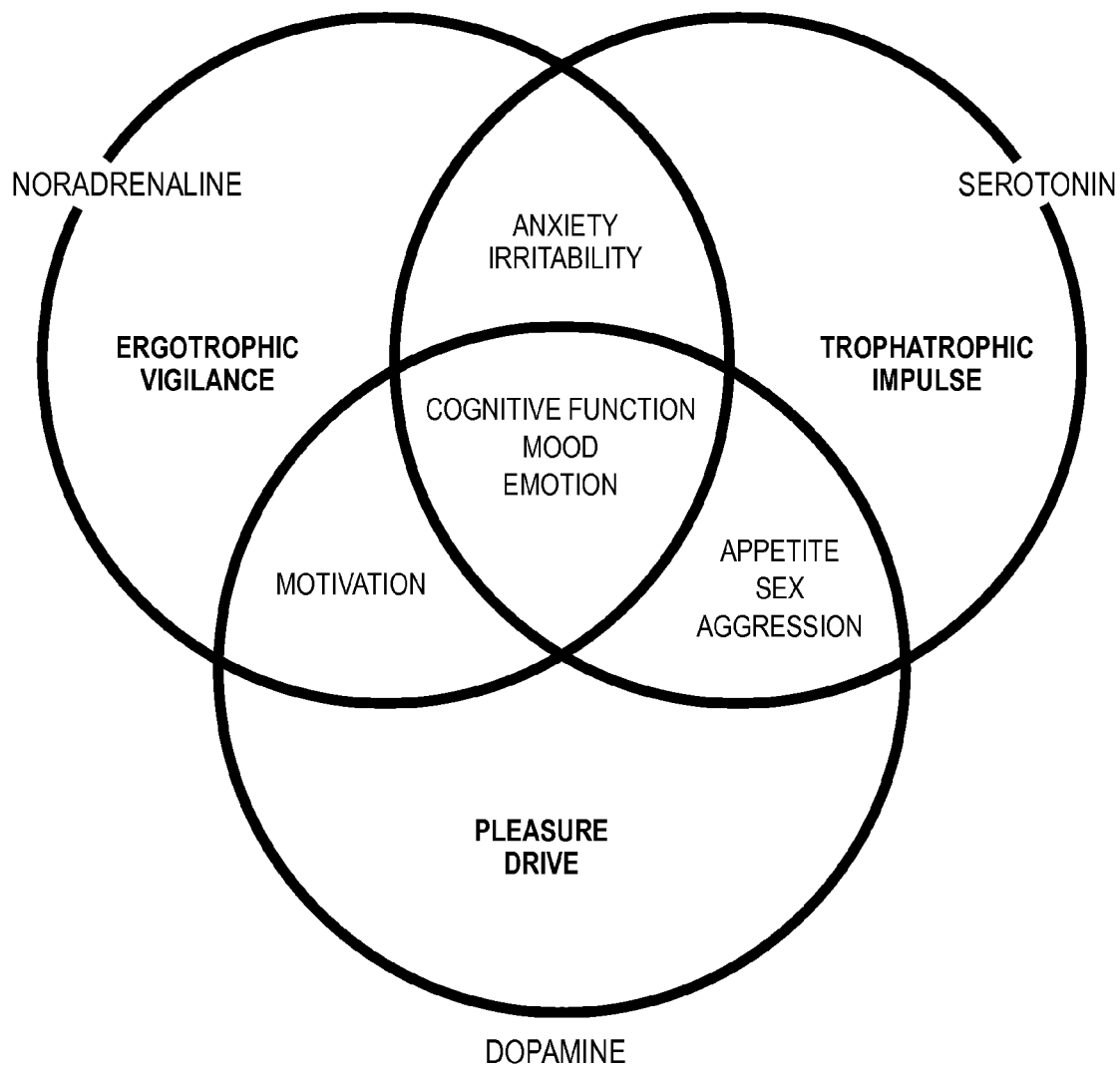

INTEGRATED NEUROMODULATION SYSTEM FOR MOOD ENHANCEMENT OF A LIVING HUMAN SUBJECT

CROSS-REFERENCE TO RELATED APPLICATIONS

This application claims priority from U.S. Provisional Patent Application Ser. No. 61/709,501, filed on Oct. 4, 2012, entitled, "Supplement for Neurotransmitter Deficiency and Mood Enhancement," which is hereby incorporated by reference herein.

FIELD OF THE INVENTION

The present invention is concerned with the formulation of certain specifically blended compositions as an integrated neuromodulation system and is directed to the use of such blended compositions in-vivo as a food or beverage supplement for initiating positive mood enhancement in a living human subject. In particular, the present invention is directed to producing positive mood enhancement through an integrated system of neuromodulation by concurrently acting upon multiple naturally occurring neurotransmitter systems which collectively result in a balanced physiologic effect for the individual person.

BACKGROUND OF THE INVENTION

The Many Purposes of Medicine

One common concern about the use of cognitive enhancement agents in the biomedical sphere is that they seemingly go beyond the traditional purpose of medicine. A continuing debate exists today over whether it is possible to draw a clear line of disengagement between a therapeutic treatment and a mere enhancement of ostensibly normal human body processes and functions; and if so, what is the true difference and meaningful distinction between them.

Regardless of this ongoing debate, it is nevertheless absolutely clear that many medicines and medical techniques—such as contraceptive medication and plastic surgery—constitute enhancements as such; and are overtly employed in a large variety of alternative treatment instances which are not intended to and thus cannot cure, or prevent, or even ameliorate a particular human pathological condition or a diagnosed abnormal circumstance. Moreover, there are also many circumstances and forms of human physiological enhancement that do not easily fit into the traditional medical model framework, such as psychological techniques and dietary changes; but which nevertheless are techniques which unquestionably produce major medical effects. For these reasons, even if a distinct boundary between therapeutics and enhancements could be agreed upon, it is unclear that such a fixed boundary would have any normative, much less clinical, significance.

A different, but related, concern is that resorting to medical or technological "fixes" will become a displacement for efforts to confront deeper social or personal problems. This kind of concern has surfaced repeatedly with particular regard to the common use of Ritalin and other medications developed to treat attention-deficit hyperactivity disorder (or "ADHD"). It has been recognized that such medications can function effectively as cognitive enhancers in healthy human adults; but their widespread abuse in the school-aged child population within the U.S. has sparked fierce debates, with some persons arguing that these medications are merely used to paper over the failings of the current public education system (i.e., by making rowdy boys calmer instead of developing teaching methods that can accommodate a wider range of individual learning styles and personal teaching needs).

However, if our modern society requires much more intellectual focusing and concentration than was previously needed by a human child to learn and receive a public school education, then it is certainly no surprise that many persons of any adult age today struggle regularly not only to meet the rigorous educational demands of the university and graduate/professional schools, but also must grapple to satisfy the evermore difficult employment requirements of the adult workplace and compete to accommodate the ever-changing styles and expectations imposed by the adult social world. Given this perspective, medically induced mood modifications and the routine use of cognitive enhancement agents for mind concentration and sharper mental focus are thus merely one exemplary extension of the human species' ability to adapt to the unforgiving strains and stresses of his self-created modern life environment.

Alternative Kinds of Neurotransmitters and their Functions

A. By conventional medical definition, neurotransmitters are the bioactive chemical agents which are released at the axons ending of neurons at the synapse. More than 60 chemicals substances have been identified to date which are postulated to function as neurotransmitters in-vivo.

It is long recognized that different types of neural cells secrete alternatives kinds of neurotransmitters. Each neurotransmitter is found and works in fairly specific CNS anatomical locations; and each has a different effect according to what it is and where it is activated. Notably, all of the major neurotransmitter types are made from particular amino acids, except for acetycholine.

Characteristically, neurotransmitters are small molecules which act rapidly in-vivo. Typically, each neurotransmitter type is individually synthesized within the neuron cytosol at the presynaptic terminals, and are absorbed by active transport into transmitter vesicles in the axon terminal. Then, each time an action potential reaches the presynaptic terminal of the neuron, a few vesicles release their neurotransmitter compound into the synaptic cleft; and this act takes only milliseconds (or even less time) to occur. The subsequent release of these neurotransmitters at the postsynaptic neurons also occurs within a millisecond. The overall effect is to increase or decrease the conductance through ion channels.

B. Neurotransmitters are bioactive compositions which exert their effect by binding to specific receptors on the neuronal postsynaptic membrane. A neurotransmitter can either 'excite' its neighboring neuron and so increase its activity; or 'inhibit' its neighboring neuron, thereby suppressing its activity.

In general, the activity of a neuron depends on the balance between the number of excitatory and inhibitory processes affecting it, and these can occur simultaneously. Most neurotransmitter receptors can be divided into two types: ligand-gated receptors and G-protein linked receptors.

Activation of a ligand-gated receptor enables a channel in the receptor to open and permits the influx of chloride and potassium ions into the cell. The positive or negative charges that enter the cell either excite or inhibit the neuron. Ligands for these receptors include excitatory neurotransmitters, such as glutamate; and, to a lesser extent, aspartate. Binding of such excitatory ligands to the receptor produces an excitatory postsynaptic potential (EPSP). Alternatively, binding of inhibitory neurotransmitter ligands, such as GABA and glycine, produces an inhibitory postsynaptic potential (IPSP). Conventionally, these ligand-gated receptors are also known as ionotropic or fast receptors.

G-protein linked receptors are indirectly linked to ion channels, via a second messenger system involving G-proteins and adenylate cyclase. These receptors are neither precisely excitatory nor inhibitory and modulate the actions of the classic excitatory and inhibitory neurotransmitters, such as glutamate and glycine. These receptors tend to have an inhibitory effect if they are linked to the Gi protein in the cell membrane, and exhibit a more excitatory effect if linked to the Gs protein. G-protein linked receptors are known as metabotropic or slow receptors; and typical examples include GABA-B, glutamate, dopamine (D1 and D2), 5-HT1A, 5-HT1B, 5-HT1D, 5-HT2A, 5-HT2C receptors.

The Different Modes of Action and Functionality For Individual Neurotransmitters A. The various kinds of neurotransmitters present alternative modes of action, and are typically divided and broadly classified into two broad groupings, which are:
(i) Excitatory Neurotransmitters: These are exemplified by glutamate, acetylcholine, norepinephrine and nitric oxide.
(ii) Inhibitory Neurotransmitters: These are exemplified by acetylcholine, norepinephrine, glycine, GABA, serotonin, and dopamine.

In this regard, it has been long recognized that some specific neurotransmitters can function in a dual capacity—i.e., these agents can act as both excitatory and inhibitory neurotransmitters. Acetylcholine and norepinephrine are vivid examples and instances of one neurotransmitter exhibiting both such capacities and functions in-vivo.

B. In addition, the known kinds of neurotransmitter are often cataloged into three categories of chemical composition, based on their stereochemical structures. The usual three categories are: the biogenic amine neurotransmitters; the peptide neurotransmitters; and the amino acid neurotransmitters.

The Biogenic Amine Neurotransmitters

Biogenic amine neurotransmitters have been studied the longest and are probably the best understood in terms of their relationship to human psychological disturbances. Among the predominant biogenic amine neurotransmitters which have been characterized are those summarily described below:

Acetylcholine: It is synthesized in the presynaptic terminal from acetyl coenzyme A and choline in the presence of choline acetyltransferases enzyme and is secreted by neurons in many areas of nervous system. Acetylcholine functions as both inhibitory and excitatory transmitter; but it is more known for its inhibitory action at some peripheral parasympathetic nerve endings—e.g., inhibition of heart by the vagus nerve. Acetylcholine is associated with muscle activation, learning, and memory. Alzheimer's type dementia in particular has been directly linked to acetylcholine function.

Norepinehprine: A substance which influences human sleep and alertness and is believed to be correlated to the fight or flight stress response. It is secreted by the terminal neurons whose cell bodies are present in the brain stem and hypothalamus. In particular, neurons secreting norepinephrine located in the 'locus ceruleus' send nerve fibers to widespread areas of brain to help in controlling the overall activity and moods of mind such as increasing the level of wakefulness.

It also acts as inhibitory as well as excitatory transmitter. Most postganglionic neurons of the sympathetic nervous system also secrete it, where it excites some organs and inhibits others.

Epinephrine: A composition usually thought of as a stress hormone managed by the adrenal system, but which also acts as a neurotransmitter for neurons in the human brain.

Noradrenaline: This is mainly an excitatory agent that induces physical and mental arousal and elevated mood. Its in-vivo production is centered in an area of the brain called the locus coreuleus, which is one of several putative candidates for the brain's 'pleasure' centre.

Dopamine: A compound which is released by neurons that originate in the substania nigra, and acts in-vivo as an inhibitory transmitter. It controls arousal levels in many parts of the brain and is vital for giving physical motivation. When levels are severely depleted, as in Parkinson's disease, people may find it impossible to move forward voluntarily. Low dopamine is also implicated in mental stasis; and thus LSD and other hallucinogenic drugs are believed to function via the dopamine system.

Glycine: It is released mainly at synapses in the spinal cord. It is the inhibitory transmitter.

Serotonin: The nuclei origination in the median raphe of the human brain stem secret serotonin. It acts to inhibit pain pathways in the cord and also functions as an inhibitor of higher regions of nervous system (which is believed to help control the mood of the persons); and has a profound effect on mood and anxiety—high levels of it, or sensitivity to it, are associated with serenity and optimism. Also, it has a role in modulating anxiety, sleep, appetite and sexuality. Serotonin reuptake inhibitors (SSRIs) are generally considered first line medications to treat panic disorder.

Nitric Oxide: It is secreted by nerve terminal present in those areas of brain which are responsible for long-term behavior and memory. Nitric oxide is synthesized instantly when needed. It changes the intracellular metabolic functions that modify the neuronal excitability.

Histamine: In-vivo, histamine is thought to influence arousal, attention and learning. It is also released in response to an allergic reaction. Antihistamines, which are commonly used to treat allergies, share the common side effects of sedation, weight gain and low blood pressure.

The Peptide Neurotransmitters

Peptide neurotransmitters are associated with mediation of the perception of pain, stimulation of the appetite, regulation of mood and other multiple functions. Abnormalities in peptide neurotransmitters have been associated with the development of schizophrenia, eating disorders, Huntington's disease and Alzheimer's disease.

Cholecystokinin (CCK): This peptide is a fairly new discovery that has received a lot of attention in the last decade. CCK increases relaxation inducing GABA while decreasing dopamine. Reported studies have linked CCK with anxiety and panic attacks in people with panic disorder.

Substance P: The study of neuropeptides actually began more than 60 years ago with the accidental discovery of substance P, a powerful hypotensive agent. The peculiar name derives from the fact that this molecule was an unidentified component of powder extracts from brain and intestine.

Chemically, Substance P is an 11-amino-acid peptide, and is present in high concentrations in the human hippocampus, neocortex, and gastrointestinal tract; hence its historical classification as a brain/gut peptide. Substance P is also released from C fibers, the small-diameter afferents in peripheral nerves that convey information about pain and temperature (as well as postganglionic autonomic signals).

Substance P is also a sensory neurotransmitter in the spinal cord, where its release can be inhibited by opioid peptides released from spinal cord interneurons, and results in the suppression of pain. The diversity of Substance P is highlighted by the finding that the gene coding for substance P also encodes a number of other neuroactive peptides, including neurokinin A, neuropeptide K, and neuropeptide γ.

Opioids: These peptides are so named because they bind to the same postsynaptic receptors activated by opium. The opioid peptides were discovered in the 1970s during a search for endogenous compounds that mimicked the actions of morphine. It was hoped that such compounds would be analgesics, and that understanding them would shed light on drug addiction.

The endogenous ligands of the opioid receptors have now been identified as a family of more than 20 opioid peptides that fall into three families: the endorphins, the enkephalins, and the dynorphins. Each member of these families is liberated from an inactive pre-propeptide compound (pre-proopiomelanocortin, pre-proenkephalin A, and pre-prodynorphin) derived from distinct genes. Opioid precursor processing in-vivo is carried out by tissue-specific processing enzymes packaged into vesicles along with the precursor peptide in the Golgi apparatus of the cells.

Opioid peptides are widely distributed throughout the human brain and are often co-localized with other small-molecule neurotransmitters (such as GABA and 5-HT). In general, these peptides tend to be depressants. When injected intracerebrally, they act as analgesics and have been shown to be involved in the mechanisms underlying acupuncture-induced analgesia. Opioids are also involved in complex behaviors such as sexual attraction and aggressive/submissive behaviors; and they have also been implicated in psychiatric disorders such as schizophrenia and autism, although the evidence for this is debated. Unfortunately, the repeated administration of opioids leads to tolerance and addiction The Amino Acid Neurotransmitters These compositions are viewed by some experts as the main players in the neurotransmission process. There are functionally two known kinds of major amino acid neurotransmitters:

Gamma-aminobutyric acid (GABA): GABA is a major inhibitory neurotransmitter that acts through a negative feedback system to block the transmission of a signal from one cell to another. It is important for balancing the excitation in the brain. The nerve terminals secrete it into the spinal cord, cerebellum, basal ganglia and into different areas of the cortex; and once there, it causes inhibition of signal from one cell to another. Benzodiazepines (anti-anxiety drugs) work on the GABA receptors of the brain, inducing a state of relaxation.

Glutamate and Aspartate: This is the human brain's major excitatory neurotransmitter, and is vital for forging the links between neurons that are the basis of learning and long-term memory. Glutamate is secreted by presynaptic terminals in many of the sensory pathways which enter the central nervous system as well as many areas of cerebral cortex. It functions as excitatory transmitter and is the most abundant chemical messenger in the brain.

It is important also to note that GABA and glutamate are carefully orchestrated to balance each other. Dysfunction of one of these amino acid neurotransmitters affects the function of the other. Some experts believe that their excitatory and inhibitory balance influences all brain cells.

C. It is well documented via the published medical literature that several different neurotransmitters can be released from a single nerve terminal as co-transmitters; and these co-transmitters often include neuropeptides and small molecule neurotransmitters. Thus, in addition to acting as neurotransmitters in their own right, neuropeptides can act as co-transmitters; and in their role of co-transmitters, they can activate specific pre- or postsynaptic receptors to after the responsiveness of the neuronal membrane to the action of 'classical' neurotransmitters, such as noradrenaline and serotonin.

Moreover, it has been long known that three particular neurotransmitters—serotonin, noradrenaline and dopamine—are intimately involved in the day to day control of many of our mental states; sometimes acting alone, and at other times acting together. This feature of overlapping control via interactions of serotonin, noradrenaline and dopamine is illustrated by FIG. 1 herein.

These three particular neurotransmitters, as well as the many other kinds of neurotransmitters known to date, play a pivotal role in the pathological basis of mental illness and diseases of the brain. Much of the evidence for this stems from the empirically proven fact that most of the effective antidepressant drugs are thought to work by changing either serotonin and/or noradrenaline metabolism, or by modifying receptor sensitivity to these neurotransmitters.

In-Vivo Neurotransmitter Imbalances

A. Neurotransmitter-related disorders occur when the current levels of neurotransmitters are unable to properly relay the electrical signal from one nerve cell (neuron) to the next. A neurotransmitter imbalance can result from the quantity levels being either too high or too low.

Clearly, neurotransmitters quantitatively exist in a delicate balance with one another in-vivo. If the levels of one or more neurotransmitters become too low, the dynamic balance in-vivo can shift and other neurotransmitter levels can become too high. Thus typically, if the quantitative levels of neurotransmitters are low, the nerves fire ineffectively or not at all. In comparison, if the quantitative levels of neurotransmitters are too high, the nerves of the CNS may fire inappropriately.

A substantial neurotransmitter imbalance can and will cause serious medical consequences. The recognized effects of substantial neurotransmitter imbalances in-vivo have been clinically linked to all of the following medical problems:

Attention issues (lack of focus and motivation, poor concentration, and ADD);
Learning difficulties and development delays (young children);
Hyperactivity and ADHD for both children and adults;
Sleeping problems (fatigue, problems falling asleep, tossing and turning, etc.);
Menopause related issues (hot flashes, mood swings, night sweats);
PMS and mood changes from oral contraception (mood swings, aggressiveness, irritability, sadness, lack of libido);
Weight issues and appetite control (cravings, overwhelming hunger, etc.);
Depression (sadness, lack of motivation, mood swings, etc.);
Migraine headaches;
Anxiety (irritability, nervous, obsessive-compulsive, insecurity, racing thoughts, restlessness);
Libido (lack of sex drive for women and men, orgasm issues, erectile dysfunction, etc.

B. Of the many factors affecting neurotransmitter balance in-vivo, four causes stand out as the most prevalent. These four predominant factors are: (i) chronic stress; (ii) poor diet; (iii) neurotoxins; and (iv) human genetics.

Chronic stress is typically the primary contributor to neurotransmitter imbalance in-vivo. Stress, both emotional and physical, can cause neurons to use up large amounts of neurotransmitters in order to help the person cope with his problems. Chronic daily stresses—varying from a busy career, to a stressed personal relationship, to a bacterial or viral infection—will tax the nervous system; and over time, deplete neurotransmitter quantities.

Poor dietary habits often lead to nervous system imbalances in-vivo, especially if the poor diet is combined with high stress. The body must synthesize the majority of its neurotransmitters from nutrients, primarily amino acids and proteins, which are obtained in the diet or through dietary supplements. However, diets with insufficient proteins or too many high glycemic carbohydrates will increase excretion of endogenous neurotransmitters. Also, diets low in Omega-3 fatty acids will routinely lead to poor neuron function, because human brain cell membranes are composed primarily of lipids and Omega-3 fats help to stabilize these membranes.

As concerns neurological toxins, there are a vast amount of environmental toxins in the world we inhabit; not to mention the use of alcohol, nicotine, and caffeine that also affect brain chemistry and nervous system health. The importance of toxin cleansing is important for every person, but especially for those individuals with neurotransmitter imbalances in-vivo.

The predisposition effect of personal genetics is also clearly established. Some individuals are intrinsically metabolically predisposed to exhibit neurotransmitter deficiencies or excesses; and these predispositions are directly attributable to one's own genetics. Also, certain kinds of health conditions, such as depression and attention deficit/hyperactivity disorder, are found to exist consistently in most if not all the members of a single family or a single set of intimately related persons. For these persons, neurotransmitter deficiencies or excesses are effectively unavoidable.

The True Value Of Cognitive Function Enhancement

Human cognition is often defined as the set of functional processes a human brain uses to receive, organize and retain information. These human cognitive brain functions typically include: acquiring information (perception); gathering and selecting (attention); representing and comprehending (understanding); retaining and recalling information (memory); and using recollection to direct and guide behavior (reasoning and coordination of motor outputs).

Interventions to improve cognitive function may be directed at any one of these core faculties; and any intervention that is aimed at correcting a specific pathology or defect of a cognitive subsystem may be properly characterized as being therapeutic in effect.

Accordingly, a cognitive enhancement is an intervention that improves brain function in some way other than repairing cells and tissues or remedying a specific dysfunction. In meaningful use and effect, therefore, any distinction between a therapy and an enhancement is often difficult to discern, and functionally lacks practical significance. For example, cognitive enhancement for a person whose present natural memory is poor might result in that person having an improved memory that is still worse than that of another individual who retains a fairly good memory despite suffering from an identified pathology (such as early-stage Alzheimer's disease). Cognitive enhancement is thus a relative term, with the point of reference always being the degree of functional capability for a single identifiable human before and after intervention.

A cognitively enhanced person, therefore, is not necessarily somebody with particularly high (let alone above average) cognitive capacities. Instead, a cognitively enhanced person is someone who has benefited from an intervention that improves the performance of at least one identifiable cognitive function without necessarily correcting an existing identifiable pathology or underlying cause for dysfunction of that cognitive ability.

The Spectrum Of Cognitive Enhancement Formats

The conventionally available range of cognitive enhancement agents include not only medical and pharmaceutical interventions as such; but also encompass psychological interventions (such as learned mental routines or mental strategies), as well as improvements via external technological and institutional structures that support cognition. A particularly distinguishing feature of all cognitive enhancement formats, however, is that they improve core cognitive capacities rather than merely concentrate upon narrowly defined skills or domain-specific knowledge.

Nevertheless, most efforts to enhance cognition today are of a rather mundane nature, and some of these techniques have been practiced for thousands of years. One prime example is education and training, where the intervention goal is often not only to impart specific skills or information, but also to improve general mental faculties such as concentration, memory, and critical thinking. Other forms of mental training, such as yoga, martial arts, meditation, and creativity courses are also in common use for this purpose.

In the main, however, most persons today prefer to use one or more physiologically active agents for cognitive enhancement.

Physiologically Active Agents Conventionally Used for Human Cognitive Enhancement A wide range of very different physiologically active agents are commonly employed today to enhance cognitive functions of the human brain; but, in general, many of these physiologically active agents are collectively and cumulatively known to have poor efficacy in humans, with typically expected failure rates of about 50% [see for example, Turner E H, Matthews A M, Linardatos E, Tell R A, Rosenthal R. Selective publication of antidepressant trials and its influence on apparent efficacy, *N. Engl J Med,* 2008, 358: 252-260; and Rubinow D R, Treatment strategies after SSRI failure—good news and bad news, N Engl J Med, 2006, 354:1305-1307].

It is noteworthy that a series of qualitatively different categories of physiologically active agents have been commonly used by humans either habitually or at least occasionally for cognitive enhancement. These individual categories include at a minimum: (1) highly potent pharmaceutical drugs and other pharmacologically active formulations; (2) the recreational illicit drugs; (3) stimulants and energy producing foods and beverages; and (4) nootropic substances. Each of these four individual categories is briefly reviewed below.

1. Highly Potent Pharmaceutical Drugs and Other Pharmacologically Active Formulations Constituting this first broad category are the compositionally defined and well characterized chemical classes of pharmaceutical drugs and other similar pharmacologically active formulations. Within this broad category, there are a range of very different and distinct classes of drugs.

By conventional medical definition, a drug is any one or more of the following: (a) a substance used as a medication or in the preparation of medication; (b) according to the Food, Drug, and Cosmetic Act, is a substance recognized in an official pharmacopoeia or formulary; (c) a substance intended for use in the diagnosis, cure, mitigation, treatment, or prevention of disease; (d) a substance other than food intended to affect the structure or function of the living body; and (e) a substance intended for use as a component of a medicine, but is not a device or a component, part, or accessory of a device Among the best known and most frequently employed of these drug chemical classes are those summarily described below. One specific class of such chemically defined pharmaceutical drugs is the Selective Serotonin Reuptake Inhibitors (hereinafter "SSRIs"), which typically include those drug formulations conventionally known today as "Prozac", "Zoloft", "Lexapro" and the like. However, this class of SSRI agent as a whole is only marginally effective as therapeutic treatments to correct neurotransmitter deficiencies; and all of the known SSRI formulations are prescription-only drugs, and thus have the added disadvantages of being expensive in cost, being of very limited tolerance in human bodies, and causing major systemic side effects [see for example: Hu X H, Bull S A, Hunkeler E M, et al., Incidence and duration of side effects and those rated as bothersome with selective serotonin reuptake inhibitor treatment for depression: patient report versus physician estimate, *J Clin Psychiatry,* 2004, 65: 959-965; Stone M B & Jones M L, Clinical review: relationship between antidepressant drugs and suicidal behavior in adults", *Overview for December* 13 *Meeting of Psychopharmacologic Drugs Advisory Committee (PDAC),* FDA, pp. 11-74; Levenson M, Holland C., Statistical evaluation of suicide in adults treated with antidepressants, *Overview for December* 13 *Meeting of Psychopharmacologic Drugs Advisory Committee (PDAC),* FDA, pp. 75-140; Olfson M, Marcus S C, Shaffer D., Antidepressant drug therapy and suicide in severely depressed children and adults: a case-control study, *Archives of General Psychiatry,* 2006, 63: 865-872; Clayton A H, Antidepressant-associated sexual dysfunction: a potentially avoidable therapeutic challenge, *Primary Psychiatry* 2003, 10: 55-61; Kanaly K A, Berman J R., Sexual side effects of SSRI medications: potential treatment strategies for SSRI-induced female sexual dysfunction, *Current Women's Health Reports,* 2002, 2: 409-416; and Fava M. Weight, gain and anti-depressants, *J Clin Psychiatry,* 2000, 61(11): 37-41].

Benzodiazepines are another distinct chemical class of pharmacological drugs; and are exemplified by the drugs "Valium", "Xanax", and "Librium". All of these agents are prescription-only drugs; and are well recognized as producing an anxiolytic effect in-vivo, by acting on the GABA cell receptors. The GABA effects produced in-vivo by this class of drugs characteristically cause significant muscle relaxation and often markedly impair human cognitive functions [see for example: Ballenger J C., Benzodiazepine receptors agonists and antagonists, In Sadock V A, Sadock B J, Kaplan H I (eds.), *Kaplan & Sadock's Comprehensive Textbook of Psychiatry* (7th ed.), Lippincott Williams & Wilkins, 2000, pp. 2317-23; Barker M J, Greenwood K M, Jackson M, Crowe S F, Cognitive effects of long-term benzodiazepine use: a meta-analysis", *CNS Drugs,* 2004, 18: 37-48; Stewart S A., The effects of benzodiazepines on cognition, *J Clin Psychiatry,* 2005, 66: 9-13; Nelson, T, McSpadden M, Fromme K, Marlatt G, Effects of alcohol intoxication on metamemory and on retrieval from long-term memory, *J Experimental Psychology,* 1986, 115; 247-254; Ginzburg R, Skeletal muscle relaxants, *Pharmacotherapy,* 2008, 28:207-13].

A third chemical class of well characterized pharmacologically active drugs are the Monoamine Oxidase Inhibitors (hereinafter "MAOs"). MOAs are active compositions which act in-vivo to block the MAO enzyme, thereby delaying the in-vivo metabolism of dopamine, serotinin, and norepinephrine at the cell receptor level. However, MOA agents are severely limited in clinical usage owing to their causing significant side effects in humans, such as hypertension and mania [see for example: Marley E, Blackwell B, Interactions of monoamine oxidase inhibitors, amines, and foodstuffs, *Adv Pharmacol Chemother,* 1970, 8:185-239; and Shopsin B & Kline N S, Monoamine oxidase inhibitors: potential for drug abuse, *Biol Psychiatry,* 1976, 11:451-456].

2. Recreational Illicit Drugs

In the second general category of commonly used active agents, the recreational illicit drugs have frequently been used by humans to cause major changes of mental state and mood enhancement. This category of active agents is exemplified by the large number of different opiates and amphetamines commonly known and illicitly sold today, all of which lead seem invariably to cause addiction in some degree in humans. Among the most commonly known of these are the following.

Amphetamine-type stimulants (such as Adderall, Dexedrine, Desoxyn, etc.) are Schedule II controlled substances in the United States, and Class B drugs in the United Kingdom, with comparable legal controls in effect in most countries throughout the world. They are prescribed for attention-deficit disorders, narcolepsy, and certain cases of obesity; and are issued to counteract fatigue and to enhance performance for pilots in the armed forces of the United States of America. These also heighten alertness, mental focus, vigilance, stamina, and sex drive. They tend to be habit-forming, and exhibit side effects with prolonged or heavy use. Personal importation of amphetamine-class drugs is prohibited in many countries, and their use for recreation or for performance enhancement without a medical prescription is likewise illegal in most countries.

LSD, a psychedelic drug. When administered at higher doses, human sensory effects seem qualitatively different. Many psychedelic drugs are purported to produce this overwhelming effect on the mind. This effect on the creative process is a phenomenon that may be due to ascending traffic in the reticular activation system, which can result in stimulus overload. LSD produces hallucinogenic and entheogenic effects at doses as low as 30-40 μg (micrograms); and may also cause cognitive shifts, as well as synesthesia. LSD sometimes spurs long-term or even permanent changes in a user's personality and life perspective.

Others examples include 4-methylaminorex; Pemoline (Cylert); Psilocybin and Psilocin; MDPV; Mescaline; and 2C-D.

3. Stimulants and Energy-Producing Foods and Beverages

As the third general category of physiologically active agents, there presently exist a surprisingly large variety of alternatively formulated stimulants and energy-producing foods and beverages all of which have attempted (at least in part) to address the human need for mood changes and cognitive enhancement.

A. One major family of such active agents is stimulants. Stimulants enhance human memory by increasing neuronal activation or by releasing neuromodulators, thereby facilitating the synaptic changes that underlie learning. Thus, the earliest known enhancer drugs were mainly nonspecific stimulants and nutrients. In antiquity for example, honey water (hydromel) was used for doping purposes.

Similarly today, nicotine is a stimulate known for its complex interaction with attention and memory occurs; and strychnine is known to be a stimulant which facilitates learning. It is especially noteworthy therefore to recognize that both nicotine and strychnine exist in meaningful quantities in commercially sold tobacco products such as cigarettes, cigars, and pipe mixtures.

Among the more commonly known and used stimulants are: Adrafinil; Caffeine; Coffee; Nicergoline; Nicotine; Methylphenidate (Ritalin); Cocaine; Dextroamphetamine (Adderall, Dexedrine); Modafinil (Provigil); Phenibut; Theophylline; Amphetamines; and Carphedon (Phenotropil).

In addition, attention is directed to the fact that a huge majority of commercially available products exemplifying and representing this family of formulations use the stimulant caffeine as their primary active ingredient. The reports in the published scientific literature have revealed that caffeine metabolites (such as paraxanthine, theobromide, and theophylline) will cross the blood-brain barrier in-vivo to cause reversible blockade of adenosine receptors in the brain; and via such blockade of adenosine receptors create a simultaneous increase for epinephrine and/or norepinephrine—which then serves as the chemical means to inhibit the need for sleep and to augment mood, alertness, and attention span in the human mind.

However, among the major drawbacks of such stimulants are: They are restricted in effect and quantitative usage by severe limitations of human tolerance; and they are restrained in their efficacy to produce a desirable positive mental state in humans, such as euphoria and pleasurable affective stimulation [see for example: Daly J W, Fredholm B B, Caffeine-an atypical drug of dependence, *Drug Alcohol Depend*, 1998, 51: 199-206; and Tunnicliffe J M, Erdman K A, Reimer R A, Lun V, Shearer J, Consumption of dietary caffeine and coffee in physically active populations: physiological interactions, *Appl Physiol Nutr Metab*, 2008, 33:1301-1310].

B. A second distinct family of active agents within this category is the energy-producing foods and beverages. It has been long recognized that both changes of food eating habits and dietary supplements can affect human cognition. For example: In order to maintain optimal functioning ability, the human brain requires a continuous supply of glucose, its major energy source. Increases in glucose availability, from the ingestion of natural sugars in food or via the supplemented presence of the acute stress hormone norepinephrine, improve human memory—with the resulting cognitive enhancement effects being particularly pronounced in highly demanding mental tasks [see for example: Nybo L, Pedersen K, Christensen B, Aagaard P, Brandt N, Kiens B, Impact of carbohydrate supplementation during endurance training on glycogen storage and performance, Acta Physiol, 2009, 197: 117-127].

In a similar fashion, creatine—a nutrient that improves energy availability in the body—appears to benefit overall cognitive performance and reduce mental fatigue for many persons. In addition, besides being an energy-producing source, food fit for human consumption can contribute to human cognition by providing those particular amino acids needed for the in-vivo production of synapse neurotransmitters; and this need is particularly critical during periods of continuing mental stress or of sustained concentration. There is also ample evidence that micronutrient supplementation increases non-verbal intelligence for some children [see for example: Ratamess N A, Hoffman J R, Ross R, Shanklin M, Faigenbaum A D, Kang J., Effects of an amino acid/creatine energy supplement on the acute hormonal response to resistance exercise, In J Sport Nutr Exerc Metab, 2007, 17:608-623; Bemben M G & Lamont H S, Creatine supplementation and exercise performance: recent findings, *Sports Medicine*, 2005, 35:107-25; Kreider R B, Effects of creatine supplementation on performance and training adaptations, *Molecular and Cellular Biochemistry*, 2003, 244:89-94; Elia J, Ambrosini P J, Rapoport J L, Treatment of attention-deficit-hyperactivity disorder, *N Engll Med*, 1999, 340:780-788; Eilander et al, Multiple micronutrient supplementation for improving cognitive performance in children: systematic review of randomized controlled trials, Am J Clin Nutr, January 2010, 91:115-130].

Merely to illustrate the range and variety of energy-producing foods and beverages, many routinely consumed food items are rich sources of substances with ostensible benefits. These include:

(i) Nuts, in particular walnuts are rich sources of alpha-linolenic acid (ALA), a type of omega-3 fatty acid.

(ii) Oily fish, such as salmon or fresh tuna are good sources of omega-3 fatty acids such as eicosapentaenoic acid and docosahexaenoic acid; and whose lack in diet has been associated with increased risk of mental illnesses such as depression, anxiety, aggressive behavior, schizophrenia, or hyperactivity in children.

(iii) Berries which contain high amounts of anthocyanins have beneficial effects. Blueberries, blackberries and raspberries are among those having the highest anthocyanin content; and these act to provide a combination of neuroprotective and neurogenesis effects.

4. Nootropic Agents

The term "Nootropic" was first coined in 1972, and is a broad title formed from the Greek words nous (mind) and trepein (to bend). Nootropics as a whole are a diverse category of agents which encompass many different compositions and formats; and often are identified by alternative names such as 'cognitive enhancers', 'smart supplements', 'intelligence boosters', 'memory enhancers', and the like. Thus, nootropics are a very broad category of physiologically active substances which are individually capable of enhancing cognition, memory, and increasing the long term health of the brain.

Many nootropic agents have an in-vivo effect of mimicking the action of synapse neurotransmitters in the brain (such as acetylcholine, serotonin. dopamine and glutamate). However, the manner in which they act and the mechanisms of action in-vivo by which they achieve these results is quite different in each instance.

Notably, some nootropic agents work by increasing the quantity of nerve growth factor and cause new nerve cell growth in the brain; other nootropic agents work by increasing the oxygen supply of the brain (i.e., they are brain specific vasodilators); still others function as short term stimulants which cause a cognitive enhancing effect when used sparingly, in very small quantities.

Requisite Criteria for Qualification as a Nootropic Agent:

For a substance to be properly classed as a 'nootropic agent', it must meet and satisfy certain physiological activity criteria, which include the following:

1. A nootropic substance should increase or improve at least one recognized cognitive brain function, such as: acquiring information (perception); gathering and selecting (attention); representing and comprehending (understanding); retaining and recalling information (memory); and using recollection to direct and guide behavior (reasoning and coordination of motor outputs).

2. A nootropic substance should protect against consequences that which can disturb or disrupt the human mental state and avoid causing changes in overt human behavior—e.g., causing hypoxia (low oxygen levels in the brain);

3. A nootropic substance should always protect the human brain from the risks of causing either chemical or physical injury to the nerve cells and neural tissues;

4. A nootropic substance should improve or increase the in-vivo efficiency of subcortical mechanisms and should the facilitation of interhemispheric flow of information;

5. A nootropic substance should demonstrate an absence of negative pharmacologic effects typical of psychotropic drugs;

6. A nootropic substance should initiate very few side effects and exhibit virtually no toxicity in-vivo.

Nootropic Families and Membership

As merely representative and illustrative of the most commonly used nootropic agents today, a short listing of specific subset families and their constituent members is provided below.

The Family Membership of Recetams

The family membership of Racetams typically include the four chemical analog compositions of Piracetam, Aniracetam, Oxiracetam, and Pramiracetam. The four main commercially available "racetam" nootropics all share a pyrrolidone nucleus, whose stereochemical structure is shown below,

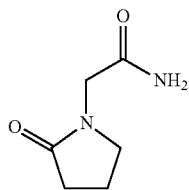

while Piracetam, Oxiracetam, and Pramiracetam also include and commonly share an acetyl group.

A. Chronologically, Piracetam was the first to be discovered (1964); and the term 'nootropic' was created to identify and distinguish its affects from other types of compositions. Piracetam (and its analogs) is a water soluble compound; and is a slight positive allosteric modulator of the AMPA receptor (i.e., Piracetam binds to the allosteric site on the AMPA receptor and may increase its functioning). Researchers are still unclear today as to Piracetam's exact mechanism of action in-vivo, but it is believed to act on ion channels in the brain leading to a general increase in synaptic transmission and excitability rather than directly acting as a neurotransmitter agonist.

Aniracetam was discovered in the 1970's; and is a fat soluble analogue of Piracetam. It's about 2×-5× stronger in effect than Piracetam on a gram for gram basis. Aniracetam is known to be a modulator of the AMPA receptor which is involved in fast synaptic transmission in the brain. Many users have reported Aniracetam to be anxiolytic (anxiety reducing in humans).

Oxiracetam is water soluble analogue discovered some time after Piracetam. It is believed to be around 5×-8× more powerful than Piracetam on a gram for gram basis. Many users of Oxiracetam report a fast onset of enhancement effects, sometimes within a few hours time. Other users of Oxiracetam commonly report a slight stimulant effect rather than an anxiolytic effect (like Aniracetam).

Pramiracetam is generally considered to be the most potent of the Racetarns. Discovered in the late 1970's, Pramiracetam (also sometimes called 'Pram' or 'Prami') is a fat soluble analog of Piracetam. On a gram for gram basis, Pramiracetam is around 5×-10× stronger than Piracetam. Some human users of Pramiracetam report having an enhanced focus and a greater clarity of thought. For others, however, Pramiracetam can be far too intense.

B. Note also that the Racetarns as a single family of member compounds (especially Piracetam and Oxiracetam) are closely related in formula and structure to the amino acid Pyroglutamic Acid. Pyroglutamic Acid itself is a discrete composition which has been shown in some studies to have weak nootropic activity. Pyroglutamic Acid is naturally present in many human foods, as well as the mammalian brain.

Each of the Racetam analogs constituting this particular family of nootropic agents provide in-vivo benefits for humans by inducing better memory retention, better memory recall, and increased acetylcholine turnover. Individual human reactions and in-vivo responses to the use of such racetams varies considerably with the individual.

The Family Membership of Chlorine Supplements

Choline is an essential nutrient needed for health promotion and disease prevention in individuals of all ages. It is essential for many of life's most basic functions including the normal functioning of all of the body's cells, brain and nerve function, liver metabolism and the transportation of nutrients throughout the body.

Acetylcholine (Ach) is a specific synapse neurotransmitter compound which is vital for learning, memory and concentration. An increased transmission of Acetylcholine in the synapse of nerve cells (neurons) demonstrably facilitates human memory, concentration, focus, and high-order thought processes (such as abstract thought, mental calculation, innovation, etc.). Acetylcholine synapse transmission in-vivo is also conventionally known as 'cholinergic' transmission, because Choline is a required component in and thus is vital for the in-vivo synthesis of the bioactive neurotransmitter Acetylcholine.

Cholinergics are, by common medical definition, substances that affect the neurotransmitter acetylcholine, or the components of the human nervous system that use or rely upon acetylcholine. In the reported scientific literature, numerous studies have shown that the purposeful extraneous introduction of various Choline supplements serve to support the normal functions of the human brain.

Thus, it is recognized that increasing the in-vivo availability of the neurotransmitter Acetylcholine within the brain cavity may sometimes improve neural functions and increase the duration of mental alertness and concentration. Nevertheless, it is also well documented and recognized in the published medical literature that markedly oversupplying the human brain with extraneous Acetylcholine will cause a directly opposite effect in-vivo—i.e., the in-vivo oversupply of Acetylcholine will markedly reduce, rather than improve or increase, human cognitive functions and performance.

A diverse range of Choline supplements is conventionally known and commonly available. Among the better known types and kinds of Choline supplements which are today commercially sold are the following.

(i) Choline precursors of acetylcholine. These typically include: Alpha-GPC (L-alpha glycerylphosphorylcholine); Choline alfoscerate; Citicoline; Choline bitartrate; and Choline citrate.

(ii) Cerebral Vasodilators. These typically include: Gingko Biloba and Vinpocetine.

(iii) Nerve Growth Stimulators. These typically include: Acetyl L-Carnitine (ALCAR); and Lion's Mane mushroom.

The Family membership of Dopaminergics

A. Dopaminergics are a family of bioactive substances that affect the synapse neurotransmitter Dopamine or the components of the nervous system that use Dopamine (DOPA) as a neurotransmitter.

Noteably, Dopamine (whose chemical formula is $C_6H_3(OH)_2$—$CH_2$—$CH_2$—$NH_2$) is a member of the catecholamine chemical family; and is a natural forerunner to and precursor compound for the synthesis of epinephrine (adrenaline) and norepinephrine (noradrenaline) in the human body. Dopamine itself as a disnct chemical composition is synthesized in-vivo via the decarboxylation of L-DOPA by aromatic-L-amino-acid cecarboxylase.

Dopamine is a naturally existing neurotransmitter precursor used in-vivo to activate specific (dopamine) receptors present upon certain kinds of neurons in the brain tissues. The hypothalamus also synthesizes and releases it as a neurohormone, with its main function then being the inhibition of prolactin release from the anterior pituitary lobe.

In its role as a natural neurotransmitter precursor, Dopamine has a wide variety of applications in the brain. In particular, dopamine markedly affects the way the brain controls human movement; and a continuing shortage of dopamine in-vivo ultimately results in Parkinson's disease. Moreover, dopamine controls the flow of information to the frontal lobe from other parts of the brain.

Disorders in dopamine levels of the brain cause declines in neurocognitive functions like memory, attention, and problem-solving. Clinically, an increase of dopamine can frequently improve the symptoms of people suffering from Parkinson's disease and other related neurological disorders. However, dopamine as a whole molecule cannot itself cross the blood-brain barrier in-vivo; and consequently, injecting or orally ingesting DOPA does not allow for its travel into the brain. Instead, synthetic L-DOPA, which is a precursor to dopamine that does in fact cross the blood-brain barrier, is often used. L-DOPA is able to cross the blood-brain barrier; and after entering the human brain tissues, is there chemically altered and converted into the bioactive entity dopamine.

B. It is critical to recognize what is Dopamine's long established role in affecting human pleasure and motivation. Dopamine is markedly associated with the pleasure system of the human brain; and its continued presence in-vivo not only provides feelings of enjoyment, but also reinforces those human behavioral activities which generate those feelings. Thus, ingestion of desired foods, overt sexual activity, and similar self-rewarding human behaviors and social experiences cause an added release of Dopamine in-vivo; and neutral stimuli associated with intense pleasure (such as indulging in sexual fantasies or fetishes) and the self-administration of certain recreational drugs also initiate dopamine synthesis and release in-vivo.

By common knowledge, the family membership of the Dopaminergic nootropics encompasses and includes all the conventionally known precursor compounds which can be employed to synthesize the bioactive dopamine molecule. Merely exemplifying this membership are the following representative substances: Mucuna pruriens (a seed powder); Tyrosine (a precursor); Phenylalanine (a precursor); Levodopa (L-dopa); Yohimbe (a type of tree bark); Selegiline (L-depreny); Tolcapone (an inhibitor of COMT); and Theanine (an extracted ingredient of tea).

The Family of Serotonergics

Serotonergics are substances that specifically affect the synapse neurotransmitter serotonin or the components of the nervous system that use serotonin as a bioactive molecule in-vivo.

Serotonoin is known to control human mood, sleep and appetite; and is produced naturally within the human body by exposure to the rays of the sun. Also, certain foods are naturally high in serotonergics that make you sleepy or that make you feel good after eating them. For instance, turkey contains very large quantities of the serotonin precursor L-Tryptophan.

By definition therefore, the family membership of Nootropic Serotonergics encompass and include all Serotonin precursors as well as the true bioactive molecular entity 5-HTP.

Among the better known and conventionally available serotonergics are the following: *Griffonia simplicifolia*; and Tryptophan (a precursor compound).

Other Diverse Family Varieties

As exemplary of these highly diverse nootropic member substances, a representative and listing typically encompasses and includes all of the following: Ashwagandha (*Withania somnifera*), a root also known as Indian ginseng; Inositol, a sugar; Kava kava, a root; Lemon balm (*Melissa officinalis*), a herb; Passion Flower; Rhodiola Rosea, a herb; St John's Wort, a herb; Siberian Ginseng (*Eleutherococcus senticosus*), a root; *Sutherlandia frutescens*, a herb; Theanine, an amino acid found in tea; Tianeptine, an anxiolytic antidepressant; Vasopressin, a hormone; Niacin, a vitamin; Picamilon (also known as nicotinoyl-GABAm, Pycamilon, or Pikamilon), a dietary supplement formed by combining Niacin with GABA; and Grape Seed (*Vitis vinifera*).

SUMMARY OF THE INVENTION

The present invention as a whole encompasses and includes a non-prescription blended formulation suitable for oral ingestion by a living human subject, and which after ingestion is able to induce a more positive mood for and to initiate an observable enhancement of cognitive functions in a living human subject.

One aspect of the invention provides a minimalist blended formulation comprising:

a controlled admixture of five types of essential active ingredients, each of which is able to cross the blood-brain barrier in-vivo, wherein said controlled admixture of essential active ingredients is limited to (a) not less than two different naturally existing nootropic dopamine neurotransmitter agonists, each of which is present in an individual quantity ranging from about 10 mg/L to about 3000 mg/L, (b) not less than one naturally existing nootropic acetylcholine neurotransmitter agonist which is present in an individual quantity ranging from about 10 mg/L to about 1500 mg/L, (c) not less than one naturally existing nootropic serotonin neurotransmitter agonist which is present in an individual quantity ranging from about 10 mg/L to about 1600 mg/L, (d) not less than one naturally existing nootropic gamma-aminobutyric acid neurotransmitter agonist which is present in an individual quantity ranging from about 10 mg/L to about 5000 mg/L, and (e) not less than one nootropic adenosine antagonist which is present in an individual quantity ranging from about 10 mg/L to about 1000 mg/L, wherein the neurotransmitter replenishment balance factor for the admixture of essential active agents mathematically is zero ("0") in value.

A second aspect of the invention also provides a non-prescription blended formulation suitable for oral ingestion by a living human subject, and which after ingestion is able to induce a more positive mood for and to initiate an observable enhancement of cognitive functions in a living human subject.

This second aspect of the invention provides a maximal blended formulation comprising:

a controlled admixture of five types of essential active ingredients, each of which is able to cross the blood-brain barrier in-vivo, wherein said controlled admixture of essential active ingredients is limited to (a) not more than six different naturally existing nootropic dopamine neurotransmitter agonists, each of which is present in an individual quantity ranging from about 10 mg/L to about 3000 mg/L, (b) not more than four different naturally existing nootropic acetylecholine neurotransmitter agonist, each of which is present in an individual quantity ranging from about 10 mg/L to about 1500 mg/L, (c) not more than three different naturally existing nootropic serotonin neurotransmitter agonist, each of which is present in an individual quantity ranging from about 10 mg/L to about 1600 mg/L, (d) not more than three different naturally existing nootropic gamma-aminobutyric acid neurotransmitter agonist which is present in an individual quantity ranging from about 10 mg/L to about 5000 mg/L, and (e) not more than three different nootropic adenosine antagonist which is present in an individual quantity ranging from about 10 mg/L to about 1000 mg/L, wherein the neurotransmitter replenishment balance factor for the admixture of essential active agents mathematically is zero ("0") in value.

BRIEF DESCRIPTION OF THE DRAWING

The present invention can be more easily understood and better appreciated when taken in conjunction with the accompany Drawing, in which FIG. 1 is a graphic representation of the conventionally known overlapping inter-relationships for the three naturally occurring neurotransmitters dopamine, acetylcholine and serotonin.

DETAILED DESCRIPTION OF THE INVENTION

Depression and depressed mood negatively affect human cognitive performance. Feelings of sadness, guilt, helplessness, hopelessness, anxiety, and fear caused by depression detract from productive thought; while apathy, being a lack of motivation, drives and affects human moods such as curiosity, interest, and determination. Other indications and symptoms which reflect human mood and influence human cognitive performance include disturbed sleep patterns, mental fatigue and loss of energy, trouble concentrating or making decisions; as well as a generalized slowing and obtunding of cognition, including memory. Clearly then, modifying human mood causes marked improvements in intelligence and mental performance.

Mood disorders are believed to afflict 60% of the world population and to be related to neurotransmitter function which can be variable according to age, dietary deficiencies, heredity, environmental stress, and hormonal imbalances. Neurotransmitter dysfunction is thus multifactorial, but typically includes several mechanisms including: insufficient production, deactivation by enzymes at the receptor level, an imbalance of neurotransmitters, poor reabsorption or uptake, and improper synchronization and timing between neurotransmitter release and receptor uptake.

For these reasons, the present invention relies upon and utilizes an entirely new concept of human mood enhancement via the concept of "an integrated neuromodulation system". In this unique approach and concept, five different classes of 'neuromodulatory' brain neurotransmitters (all of which are naturally existing the central nervous system) are successfully integrated and employed collectively to produce positive mood enhancement for the individual person.

Via such integrated neuromodulation, the invention takes advantage of the fact that one particular kind of neuron can use multiple different neurotransmitters concurrently to connect to and activate several other neurons in the same anatomic locale. Such alternative neuromodulatory transmitter agents are typically synthesized and released by a small select group of neurons dispersed in-vivo over large anatomic areas of the central nervous system. Each of these select neurons has an effect upon multiple adjacently located neurons; and consequently these select neurons have the unique capability of activating many other neurons concurrently and collectively.

These select neurotransmitter systems are thus sets of select neurons in the brain, which are able to express activity effects in large volumes of the brain, or in volume transmission. This select neuron capability and event stands in marked difference and contrast to the more usual single direct electrical synaptic transmission, in which one presynaptic neuron directly influences a postsynaptic partner, such as a single neuron reaching to one other neuron.

The "Integrated Neuromodulation" Effects Initiated by the Invention

In view of the foregoing, the present invention intentionally accesses and employs five discrete and naturally existing neurotransmitter systems in combination for implementing "integrated neuromodulation" in-vivo; and these are: the dopamine, serotonin, acetylcholine, gamma amino butyric acid, and adenosine systems. In order to recognize and appreciate properly what are the beneficial effects of implementing such an "integrated neuromodulation", the following points of information are deemed to be particularly valuable.

(1) Neurotransmitter agents are deemed to be either excitatory or inhibitory in their actions, and exert their in-vivo activity through receptor sites at the synapse of the receiving neuron. In the present invention, the targeted excitatory neurotransmitter systems specifically are the dopamine receptors and adenosine receptor blockade; while the targeted inhibitory neurotransmitter systems specifically are acetylcholine, serotonin, and gamma aminobutyric acid receptors.

(2) Volume transmission is the process of activation of neurotransmitter systems on large portions of the brain. The volume transmission concept is based on empiric evidence that the brain attempts to compensate for deficiencies in neurotransmitter systems; but that the end physiologic result is not precise, leading to compensatory stimulatory or inhibitory activity. Furthermore, neurotransmitter systems are interrelated, with multiple regulatory functions. This concept will become evident in the neuromodulary hypothesis, the centerpiece of this invention, as the central role in mood enhancement.

(3) Dopamine is the major stimulatory neurotransmitter of the brain and is 3 to 4 times more abundant when compared to acetylcholine neurotransmitter, which is inhibitory. However, the number of dopamine neurons in the brain is limited, and is estimated at only about 30,000 to 40,000 in total, with a loss of 13% per decade of life.

Also, dopamine is receptor site specific. For instance, dopamine produced in the caudate nucleus facilitates posture, whereas dopamine in the nucleus accumbens of the frontal cortex is associated with rapidity of movements and pleasure. These areas connect with the substantia nigra of the midbrain, which produces 80% of all dopamine in the brain.

As to its effects, dopamine produces feelings of psychological energy and sexual arousal, with diminished appetite and need for sleep. Addicting drugs (such as cocaine and amphetamines) produce a dopamine excess, which can lead to permanent neuronal death and the consequence of losing the capability for normal human pleasure responses. Furthermore, Parkinson's disease is the clinical result of degeneration of the substantia nigra of the brain—thereby resulting in dopamine deficiency, and a loss of muscle coordination and both cognitive and affective decline.

(4) Serotonin is an inhibitory neurotransmitter agent which has its greatest concentration in the pineal gland of the brain. Serotonin is an important mood stabilizer in-vivo; and acts to decrease pain sensitivity, aggressive behaviors, and libido (while also often producing weight gain).

Clinically diagnosed depression afflicts 3 to 4% of the population; and is believed to be a result, at least in part, of serotonin deficiency. Noteably, the prevalent medical practice of administering selective serotonin reuptake inhibitors (SSRIs) markedly inhibit the reuptake of serotonin neurotransmitter from the synaptic gap, thereby resulting in an increase in serotonin neurotransmitter action in-vivo.

(5) Acetylcholine is an inhibitory neurotransmitter agent with relatively few receptors in the brain (and located in the interpeduncular nucleaus near the substantia nigra of the midbrain); and where a majority of receptors are found outside the brain in the skeletal and smooth muscles controlled by the autonomic nervous system.

Acetylcholine produces REM sleep and is also important in memory retention. Clinically, Alzheimer's disease is caused by a loss of cells in the basal forebrain that secrete acetylcholine, resulting in memory loss as well as a diminution of sensory and associative information for processing and motor activities.

(6) Gamma amino butyric acid ("GABA") is the major inhibitory neurotransmitter of the brain which is present in 30 to 40% of all brain synapses, and highly concentrated in the substantia nigra of the midbrain, basal ganglia, hypothalamus, and hippocampus. GABA concentrations in the brain are estimated to be 200 to 1000 times that of either dopamine or acetylcholine.

In vivo, GABA produces smooth muscle relaxation; and can counteract the muscle hyperactivity associated with dopaminergic stimulation. Anxiety is the most prevalent worldwide psychiatric disorder, affecting 10 to 30% of people; and GABAergic agents—such as alcohol, barbiturates, and benzodiazepines—are very prevalent for recreational use.

(7) Adenosine receptors are present in high levels in the central nervous system of the body. Activation of Adenosine receptors in the brain slow metabolic activity and also affect the sleep-wake cycle.

A blockade of Adenosine receptors produces the reverse effect—i.e., warding off drowsiness and restoring alertness—in addition to initiating other stimulatory effects, such as faster and clearer flow of though, increased focus, and improved body coordination. Stimulatory effects on the peripheral nervous system include muscle tremor and twitching.

(8) The present invention notably relies upon the use of nootropic agents as the active ingredients for implementing "integrated neuromodulation" in-vivo. Nootropic agents can produce an immense range of effects on human mental functions, including but not limited to: cognition, memory, intelligence, motivation, attention, and concentration. These nootropic agents can work by a number of mechanisms including neurotransmitter replenishment, enzyme expression, and/or hormonal function, brain vascularity, and nerve growth. Moreover, many of these nootropic agents can cross the blood-brain barrier in order to produce psychoactive effects; and it is precisely for this reason that in the present invention, only naturally occurring nootropic agents are used to implement "integrated neuromodulation" for five discrete neurotransmitter systems.

I. The Blended Formulations of the Invention as a Whole

It is noteworthy that the full range and variety of blended formulations constituting the present invention can be used by any living human subject (but preferably by adults rather than children) to achieve the desired effect of markedly modifying the attitudes, perceptions, and observed social behaviors for such persons. In particular, the purposely blended formulations can and will perform three related, but distinct, function in-vivo, which are:

($\alpha$) Cause a series of distinct biochemical changes in-vivo; which in turn will ($\beta$) Initiate psychological consequences in that person; and which in turn will ($\gamma$) Induce an observable increase in cognitive functions for that living human subject.

Each of these is described in meaningful detail below.

($\alpha$). The present invention uses a balanced neurotransmitter neuromodulatory effect to produce a clinically significant effect in humans. This is empirically demonstrated herein via human clinical studies which use a combination of low doses of five individual types of nootropic neurotransmitter agents as a blended formulation which causes a series of distinct biochemical changes in-vivo. The orally ingestible blended formulation is always a prepared admixture of five alternative classes of nootropic agents in low dose amounts which are neuroselective and will cross the human blood-brain barrier to produce concurrent stimulation of dopamine, serotonin, GABA, and acetylcholine receptors, with simultaneous reversible adenosine receptor blockade; which result in a clinically significant 'balanced neurotransmitter volume transmission'.

This balanced neuromodulation of neurotransmitter systems produces a desirable mood enhancement state of temporary euphoria and pleasure in the human without depleting other kinds or sources of neurotransmitters—a severe limiting side effect and major drawback of current practices which use conventional pharmacologic agents, energy drinks, and recreational drugs. The blended formulations administered in low dose amounts also are believed to have a protective effect at the brain neurotransmitter receptor level and will produce the optimum level of physiologic effect, while minimizing undesirable side effects and systemic effects in the body. Also, because the blending of five different classes of nootropic agents are naturally existing food elements which the body needs to produce the optimum level of neurotransmitter supply, whatever the human body does not need or use, it will eliminate.

(β). The psychological events initiated within the person will generate a positive change in one's personal perceptions; evoke optimism as the subjective state of mind; and elicit a more sociable attitude and favorable mood as the observable behavior of the affected human person.

This more positive mental state of and better mood for the person stands in stark contrast and difference to the usual anxiety and mental anguish usually experienced by that person when confronted with mental tasks of any consequence; is a significant betterment of the person's typical peace of mind and mental comfort; constitutes a meaningful reduction of the person's phobias, apprehensions, and fears (whether justified or not); and results in a more favorable and gentler pattern of observed social behaviors.

Furthermore, it should be recognized also that, once the person has experienced such an increase in positive mood and enjoyed a true reduction of his existing apprehensions and fears; that individual will retain the memory of having had a more pleasant mental state of mind, as well as having felt more at ease with himself and the world at large. This personal memory and recollection of a pleasant and more positive experience will typically cause that individual to reconsider the need or worth of his prior negative feelings, and encourage that person to recreate and regenerate for himself a more favorable mood and positive mental state again and again—as a protection for and safeguard against the next possible occurrence of anxiety, apprehensions, and fears.

Certainly for those persons who are frequently apprehensive or often uneasy in their minds, the value and benefit of having a prepared in advance, oral ingestable blended supplement which can overcome one's anxieties and overtly increase the motivation of and positive propensity for the individual to grapple with controlling his own mental state— is both a comfort and a relief—to the degree that the individual becomes mildly comfortable, if not enthusiastic, about his mental attitudes and thought processes. In contrast, even for those blessed persons whose typical attitude and state of mind is merely neutral or truly dispassionate in their moods, such persons will have the benefit and distinct advantage that an orally ingestible blended supplement is available as a temporary stop-gap measure should they find themselves in unusually difficult or overwhelming life circumstances.

(γ). In addition to the initiation of a more positive state of mind, the other major result and effect of ingesting the blended supplement is an observable amplification of human brain functions and a measurable increase of human concentration, focus and memory. Thus, the blended supplement can and will induce an observable and objectively determinable enhancement of cognitive functions in the individual—i.e., improve the functional processes a human brain uses to receive, organize and retain information.

The improvements in human cognitive brain functions will typically include: acquiring information (perception); gathering and selecting (attention); representing and comprehending (understanding); retaining and recalling information (memory); and using recollection to direct and guide behavior (reasoning and coordination of motor outputs). Accordingly, the major result and true effect of orally ingesting the blended supplement is an observable amplification of human brain functions and a substantive increase of human concentration, focus and memory.

The ingestable blended supplement is thus beneficial for and advantageous to those persons who have a fear or dread (often groundless and typically unfounded) of a failing memory and/or a loss of mental alertness and awareness. Consequently, the ingestable blended supplement concomitantly induces an observable and overt change in human behaviors which reflect enhanced cognitive functions and an improved memory recall.

Accordingly, among the true benefits and unexpected advantages offered by the invention is a more favorable perception by the person that he can focus, concentrate and remember—and thus not only cope but also succeed when confronted with and/or subjected to the stresses and problems of everyday life.

II. Definitions[#]

Although many of the words, terms and titles employed herein are commonly employed and conventionally understood in their traditional usage and context by persons ordinarily skilled in this art, a short listing of definitions is presented below in order to provide at least a minimal vocabulary of common usage; and to serve as an aid and guide for avoiding misinformation, misunderstandings, and ambiguities in titles and terminology which often exist in this technical field; and to introduce specialized terms and particular jargon for recognizing and distinguishing among the details of the present invention; as well as for appreciating the true scope and breadth of the claims recited herein.

The Human Brain: Anatomically, the cerebrum, cerebellum, and medulla oblongata—all of which lie within the cavity space of the cranium.

Human Cognition: The mental processes a human brain uses to organize information. This range of mental processes include acquiring information (perception), selecting (attention), representing (understanding) and retaining (memory) information, and using it to guide human behavior (reasoning and coordination of motor outputs).

Human Cognitive Enhancement: The amplification or extension of core mental capacities of the human brain through improvement or augmentation of internal or external information processing systems.

Cognitive Enhancer Agents: A set of often diverse compositions and formulations that can amplify human concentration and increase human memory in-vivo.

Nootropic substances: A distinct subset of biochemical entities within the Cognitive Enhancer Order of bioactive compositions that are characterized by being functionally cognitive enhancing, being neuroprotective, and being extremely non-toxic in humans in-vivo. All nootropic substances are by definition cognitive enhancer agents—but not every cognitive enhancer agent is properly a nootropic substance. Thus, all nootropic substances as a distinct subset of bioactive agents are purported to be or have been empirically shown to be able to enhance human concentration and/or increase human recollection and the formation of memories. Furthermore, all nootropic substances are individually and collectively functionally capable of crossing the human blood-brain barrier in-vivo after being introduced as an extraneous agent, and therein demonstrate their psychoactive properties upon the neurons then existing in the human brain.

Agonist: A substance that acts like another chemical composition and therefore excites or stimulates an action in-vivo. An agonist is a primary bioactive agent in the dynamic systems of the human body and in its pharmacology; and is the direct opposite of an antagonist.

Neurotransmitter agonist: A bioactive agent which increases the production of the neurotransmitter or neurotransmitter precursors in a living subject in-vivo, and/or increases the number of neurotransmitter receptors at the synaptic level to increase neurotransmitter expression.

Antagonist: A chemical substance that interferes with the physiological action of another, especially by combining with and blocking its nerve receptor.

Adenosine antagonist: A bioactive agent which decreases or inhibits the expression of an recognized effect or result of the nucleoside Adenosine in-vivo.

For further explanations and definitional details, please see: Goodman & Gillman Saunder's Medical Dictionary Chamber's Technical Dictionary

III. The Underlying Principles of the Invention

The unique concept of the present invention is controlled and demonstrated by four underlying principles, which are:

The $1^{st}$ Principle: Five and only five naturally occurring neurotransmitter systems (designated herein as $N_1$, $N_2$, $N_3$, $N_4$, and $N_5$ respectively) must be involved in order to produce a balanced neuromodulation of the affective neural centers of the brain. This principle is based on a volume transmission of multiple neurotransmitter systems simultaneously; and also assumes the presence of select neural cross-communication between different neurotransmitter systems.

It is therefore imperative in this neuromodulation process that all five individual neurotransmitter agent classes be activated together concurrently in order to produce a positive mood enhancement for the person. As part of this process, if one or more neurotransmitter system constituents ($N_1$ through $N_5$) are missing, then this omission will cause a failure of the blended formulation to initiate positive mood enhancement in-vivo in a consistent and reliable manner.

It is critical to understand and appreciate also that, although more than sixty neurotransmitter systems are currently known to exist in the human body, five and only five naturally occurring neurotransmitter systems (designated as N1, N2, N3, N4, and N5 respectively) are employed by the present invention to produce a balanced neuromodulation of the affective neural centers of the brain. In particular, no other neurotransmitter agonistic or antagonistic agents of any kind, functional capacity, chemical composition, or stereochemical structure can be added nor should be included in the blended formulation as an essential active ingredient at any time, for any purpose. According, there is always a complete absence and lack of any other nootropic neurotransmitter agonist(s) or antagonist(s) except for the requisite five classes of active ingredient agents, which are overtly limited to: at least one dopamine agonist, a neural stimulant; at least one acetylcholine agonist, a neural inhibitor; at least one serotonin agonist, a neural inhibitor; at least one GABA agonist, a neural inhibitor; and at least one adenosine antagonist, a neural stimulant.

The $2^{nd}$ Principle: It is noted that in order to affect all five neuromodulatory systems concurrently, the volume transmission of the five different classes of neurotransmitter agents is not equal throughout the human body. Instead, neuromodulation is dominated by inhibitory neurotransmitters system agents such as acetylcholine, serotonin, and gamma aminobutyric acid—thereby producing an overall inhibitory effect (in contrast to an excitatory effect). Consequently, the type number ratio of individual neurotransmitter agent expression is important, and the type number ratio of the different classes of agents must be tightly controlled in order to produce a positive state of mood enhancement.

The practice and implementation of this $2^{nd}$ principle is performed in the following manner: The present invention demands that the proper balance of volume expression of neurotransmitter system agents should yield a net balance of zero in order to produce mood enhancement which is neither excitatory nor inhibitory (i.e., $\Delta N=0$). This principle is designated as the Neuromodulary Hypothesis, and is expressed by the formula:

$$\Delta N = [N_1 + N_2 + N_3 + N_4 + N_5] = 0$$

where $N_X$ is the net effect of those individual neurotransmitter system agents which are excitatory/stimulatory (+1, +2, +3 . . . ) versus those agents which are inhibitory/relaxant (−1, −2, −3 . . . ) in producing volume neurotransmission.

As part of this Neuromodulary Hypothesis, if the net balance ($\Delta N$) of all the individual neurotransmitter system agents present as part of any formulation is not at parity ($\Delta N \neq 0$), then an agent imbalance is created which is either stimulatory or inhibitory in effect; and this in turn will cause a failure to initiate positive mood enhancement in a reliable manner.

The $3^{rd}$ Principle: The weight-to-volume ratio of all the individual neurotransmitter system agents is employed to fine-tune the stochiometric quantities of the discrete nootropic substances in each admixture of active ingredients. The weight-to-volume ratio of all the individual neurotransmitter system agents will reflect specific boundaries and parameters of each blended formulation embodying the present invention. Consequently, the weight-to-volume ratio of all the individual neurotransmitter system agents in any formulation must meet and satisfy specific range limits.

Another aspect of this $3^{rd}$ principle is that preferred quantities of individual neurotransmitter system agents will reflect certain necessary physiologic effects associated with a particular neurotransmitter system. For instance, exceeding a set and limited quantity of specified nootropic agent may not result in achieving the desired physiologic result. As one illustration of this point, doubling the amount of an agent $N_X$ from 1 to 2 units cannot and does not necessarily produce double the physiologic effect. Instead, in such instances, it is instead the addition of another nootropic agent $N_Y$ which acts to augment and increase the effects of agent $N_X$ in a synergistic manner, even with very small quantity units or doses of the individual agents—thereby resulting in a physiologic result which is greater than the sum of the physiologic effects of the two individual components $N_X$ and $N_Y$.

The $4^{th}$ Principle: If nootropic agents components $N_X$ and $N_Y$ do not result in a symbiotic and synergistic physiologic result which is greater than the overall effects of using $N_X$ and $N_Y$ individually, then this outcome will cause a failure of positive mood enhancement to occur in the person in a consistent and a reliable manner.

Also as a direct corollary, the stochiometric quanitites of the five different classes of nootropic agents have particular relevance to the efficacy of agent combinations which are synergistic in their effects despite having alternative mechanisms of action. For instance, overloading certain neurotransmitter system agents can result in an opposite and wholly unwanted effect, by depleting these brain neurotransmitters over time. Notable examples of this phenomenon include caffeine, amphetamines, and cocaine.

For these reasons, in the blended formulations of the present invention, the five classes of active ingredient agents are overtly limited to: at least one dopamine agonist, a neural stimulant; at least one acetylcholine agonist, a neural inhibitor; at least one serotonin agonist, a neural inhibitor; at least one GABA agonist, a neural inhibitor; and at least one adenosine antagonist, a neural stimulant. This is represented by a type number ratio of [1:1:1:1:1].

However, a very different type number ratio should be employed in order to achieve consistent and reliable results in-vivo. Accordingly, the range of truly functional type number ratios starts with a minimal ratio of [2:1:1:1:1] and extends to a maximal ratio of [6:4:3:3:3]. The net physiologic result of restricting these type number ratios to such specified limits is a balanced neurological enhancement.

Iv. Requisite Active Ingredients of the Blended Formulations

Each and every embodiment of the orally ingestable blended formulation must comprise not less than five (5) different bioactive ingredients in dry or fluid admixture. These five discrete bioactive ingredients are:

(i) At least one naturally existing nootropic dopamine neurotransmitter agonist in a preferred quantity ranging from about 0.01 g to 3.0 g;

(ii) At least one naturally existing nootropic acetylecholine neurotransmitter agonist in a preferred quantity ranging from about 0.01 g to 1.5 g;

(iii) At least one naturally existing nootropic serotonin neurotransmitter agonist in a preferred quantity ranging from about 0.01 g to 1.6 g;

(iv) At least one naturally existing gamma-aminobutyric acid (GABA) neurotransmitter agonist in a preferred quantity ranging from about 0.01 g to 5.0 g; and (v) At least one naturally existing nootropic adenosine antagonist in a preferred quantity ranging from about 0.01 g to 1.0 g.

Descriptive details for each of these five bioactive ingredients are provided below.

It is critical to understand and appreciate also that, although more than sixty neurotransmitter systems are currently known to exist in the human body, five and only five naturally occurring neurotransmitter systems (designated as N1, N2, N3, N4, and N5 respectively) are employed by the present invention to produce a balanced neuromodulation of the affective neural centers of the brain. In particular, no other neurotransmitter agonistic or antagonistic agents of any kind, functional capacity, chemical composition, or stereochemical structure can be added nor should be included in the blended formulation as an essential active ingredient at any time, for any purpose. According, there is always a complete absence and lack of any other nootropic neurotransmitter agonist(s) or antagonist(s) except for the requisite five classes of active ingredient agents, which are overtly limited to: at least one dopamine agonist, a neural stimulant; at least one acetylcholine agonist, a neural inhibitor; at least one serotonin agonist, a neural inhibitor; at least one GABA agonist, a neural inhibitor; and at least one adenosine antagonist, a neural stimulant.

1. The Naturally Existing Nootropic Dopamine Neurotransmitter Agonist(s)

In the present invention, naturally occurring nootropic dopamine agonists are employed as one type of active ingredient; and these are bioactive naturally occurring substances that mimic or function similarly to the known neurotransmitter dopamine or those particular components of the central nervous system that use dopamine as a neural synapse agent. The attributable effects of dopamine are enhancement of attention, alertness, and antioxidant activity. Accordingly, each nootropic dopamine agonist will provide one or more of these well established dopamine functional attributes and capabilities.

Consequently, any and all naturally occurring dopamine neurotransmitter agonists—which are either precursor compounds or are themselves a bioactive molecule—are individually and collectively suitable for use as a first essential and critical ingredient in the admixture constituting the blended supplement. Among the preferred examples of acceptable and suitable naturally occurring nootropic dopamine neurotransmitter agonists are: L-phenylalanine; L-tyrosine; N-acetyl-L-tyrosine; L-3,4-dihydroxyphenylalanine (L-DOPA); phenylethylamine; S-adenosyl-methionine; biopterin; aminoptine; methylphenidate; selegiline; rasagiline; rhodiola rosea; ropinirole; pramipexole; mucuna pruriens; modafinil; and citicoline.

In the expected and intended range of blended formulations, the choices of these bioactive agents are carefully controlled as to number of different dopamine neurotransmitter agonists and their individual quantitative amounts. In the preferred embodiments, however, these particular agents are expressly limited in both numbers and aliquot amounts; and will be not less than two and not more than six different naturally existing nootropic dopamine neurotransmitter agonists in any prepared admixture of active ingredients. Also when present, each nootropic dopamine neurotransmitter agonist will appear in an individual quantity ranging from about 100 mg/L to about 6000 mg/L (weight/volume), or alternatively appear in an individual quantity ranging from about 100 mg/Kg to about 6000 mg/Kg (weight/weight).

In addition, the particular number of individual nootropic dopamine neurotransmitter agonists present in any blended formulation will be accounted for as a neurotransmitter replenishment balance factor in order that the admixture of all essential active agents mathematically is zero ("0") in value. Thus, the actual number of individual nootropic dopamine neurotransmitter agonists then present in any blended formulation will be chosen carefully and in advance to implement the Neuromodulary Hypothesis described above and expressed by the formula $$\Delta N = [N_1 + N_2 + N_3 + N_4 + N_5] = 0$$

wherein $N_1$ is the net effect of those individual dopamine neurotransmitter agonists which are excitatory/stimulatory (+1, +2, +3 . . . ) versus those other agents $[N_2 + N_3 + N_4]$ which are inhibitory/relaxant (−1, −2, −3 . . . ).

2. The Naturally Existing Nootropic Acetycholine Neurotransmitter Agonist(s)

In the present invention, naturally occurring nootropic acetylcholine agonists are employed as one type of active ingredient; and these are bioactive naturally occurring substances that mimic or function similarly to the known neurotransmitter acetylcholine or those particular components of the central nervous system that use acetylcholine as a neural synapse agent.

Acetylcholine is a facilitator of memory formation; therefore, increasing the availability of this neurotransmitter in the brain will improve cognitive functions. Accordingly, each nootropic acetylcholine agonist will provide these well established acetylcholine functional attributes and capabilities.

Consequently, any and all naturally occurring acetylcholine neurotransmitter agonists—which are either precursor compounds or are themselves a bioactive molecule—are individually and collectively suitable for use as a second essential and critical ingredient in the admixture constituting the blended supplement.

Among the preferred examples of acceptable and suitable naturally occurring nootropic acetylcholine neurotransmitter agonists are: choline; 2-dimethylaminoethanol (DMAE); meclofenoxate; alpha-glycerylphosphorylcholine (alpha-GPC); acetylcarnitine; pantothenic acid (Vitamin $B_5$); galantamine; huperzine A; donepezil; ispronicline; nicotine; and arecoline.

In the expected and intended range of blended formulations, the choices of these bioactive agents are carefully controlled as to number of different acetylcholine neurotransmitter agonists and their individual quantitative amounts. In the preferred embodiments, however, these particular agents are expressly limited in both numbers and aliquot amounts; and will be not less than one and not more than four different naturally existing nootropic acetylcholine neurotransmitter agonists in any prepared admixture of active ingredients. Also when present, each nootropic acetylcholine neurotransmitter agonist will appear in an individual quantity ranging from about 250 mg/L to about 2500 mg/L (weight/volume), or alternatively appear in an individual quantity ranging from about 250 mg/Kg to about 2500 mg/Kg (weight/weight).

In addition, the particular number of individual nootropic acetylcholine neurotransmitter agonists present in any blended formulation will be accounted for as a neurotransmitter replenishment balance factor in order that the admixture of all essential active agents mathematically is zero ("0") in value. Thus, the actual number of individual nootropic acetylcholine neurotransmitter agonists then present in any blended formulation will be chosen carefully and in advance to implement the Neuromodulary Hypothesis described above and expressed by the formula $$\Delta N = [N_1 + N_2 + N_3 + N_4 + N_5] = 0$$

wherein $N_2$ is the net effect of all the individual acetylcholine neurotransmitter agonists which are which are inhibitory/relaxant (−1, −2, −3 . . . ) versus those other agents $[N_1+N_5]$ which are excitatory/stimulatory (+1, +2, +3 . . . ) in effect.

3. The Naturally Existing Nootropic Serotonin Neurotransmitter Agonist(s)

In the present invention, naturally occurring nootropic serotonin agonists are employed as one type of active ingredient; and these are bioactive naturally occurring substances that mimic or function similarly to the known neurotransmitter serotonin or those particular components of the central nervous system that use serotonin as a neural synapse agent.

Serotonin is a neurotransmitter which contributes to human feelings of well being and calmness, with possible effects on neurogenesis; therefore, increasing the availability of this neurotransmitter in the brain will marked improve human mood and observable human cognitive functions. Accordingly, each nootropic serotonin agonist will provide these well established serotonin functional attributes and capabilities.

Consequently, any and all naturally occurring serotonin neurotransmitter agonists—which are either precursor compounds or are themselves a bioactive molecule—are individually and collectively suitable for use as a third essential and critical ingredient in the admixture constituting the blended supplement.

Among the preferred examples of acceptable and suitable naturally occurring nootropic serotonin neurotransmitter agonists are: 5-hydroxytryptophan (or 5-HTP, 5-hydroxy-L-tryptophan); S-adenosyl-methionine; pyridoxal phosphate (or PLP, pyridoxal-5'-phosphate, P5P, the active form of Vitamin B6); mesembrine; resveratrol; curcumin; piperine; harmal; rhodiola rosea; tianeptine; and L-theanine.

In the expected and intended range of blended formulations, the choices of these bioactive agents are carefully controlled as to number of different serotonin neurotransmitter agonists and their individual quantitative amounts. In the preferred embodiments, however, these particular agents are expressly limited in both numbers and aliquot amounts; and will be not less than one and not more than three different naturally existing nootropic serotonin neurotransmitter agonists in any prepared admixture of active ingredients. Also when present, each nootropic serotonin neurotransmitter agonist will appear in an individual quantity ranging from about 10 mg/L to about 1600 mg/L (weight/volume), or alternatively appear in an individual quantity ranging from about 10 mg/Kg to about 1600 mg/Kg (weight/weight).

In addition, the particular number of individual nootropic serotonin neurotransmitter agonists present in any blended formulation will be accounted for as a neurotransmitter replenishment balance factor in order that the admixture of all essential active agents mathematically is zero ("0") in value. Thus, the actual number of individual nootropic serotonin neurotransmitter agonists then present in any blended formulation will be chosen carefully and in advance to implement the Neuromodulary Hypothesis described above and expressed by the formula $$\Delta N = [N_1 + N_2 + N_3 + N_4 + N_5] = 0$$

wherein $N_3$ is the net effect of all the individual serotonin neurotransmitter agonists which are which are inhibitory/relaxant (−1, −2, −3 . . . ) versus those other agents $[N_1+N_5]$ which are excitatory/stimulatory (+1, +2, +3 . . . ) in effect.

4. The Naturally Existing Nootropic Gamma-AminoButyric Acid (GABA) Neurotransmitter Agonist(s)

In the present invention, naturally occurring nootropic gamma-aminobutyric acid (GABA) agonists are employed as one type of active ingredient; and these are bioactive naturally occurring substances that mimic or function similarly to the known neurotransmitter gamma-aminobutyric acid (GABA) or those particular components of the central nervous system that use gamma-aminobutyric acid (GABA) as a neural synapse agent.

The gamma-aminobutyric acid (GABA) receptor is an ionotropic receptor and ligand-gated ion channel; and is a major neurotransmitter in the central nervous system. Although GABA seems to produce an inhibitory effect on neurotransmitter release, GABA is not an inhibitory neurotransmitter itself—because it stimulates the GABA receptor on the neural cells of the brain; and therefore, its direct action and activity is really a stimulatory neurotransmitter function in-vivo.

Upon activation, the GABA receptor of the neuron selectively conducts chloride ion through its pore, resulting in hyperpolarization of the neuron. This in turn causes an inhibitory effect on neurotransmission by diminishing the chance of a successful action potential occurring. Mild inhibition of neuronal firing by drugs acting at the GABA receptor of the synapse causes a reduction of anxiety (an anxiolytic effect), while more pronounced inhibition typically induces general anesthesia.

On this basis therefore, increasing the availability of GABA in the human brain will cause a marked improvement of human mood and attitudes; and also induce increases of observable human cognitive functions. Accordingly, each nootropic gamma-aminobutyric acid agonist will provide these well established GABA functional attributes and capabilities in-vivo.

Consequently, any and all naturally occurring gamma-aminobutyric acid (GABA) neurotransmitter agonists—which are either precursor compounds or are themselves a bioactive molecule—are individually and collectively suitable for use as a fourth essential and critical ingredient in the admixture constituting the blended supplement.

Among the preferred examples of acceptable and suitable naturally occurring nootropic gamma-aminobutyric acid (GABA) neurotransmitter agonists are: ethanol; picrotoxin; and L-theanine.

In the expected and intended range of blended formulations, the choices of these bioactive agents are carefully controlled as to number of different gamma-aminobutyric acid (GABA) neurotransmitter agonists and their individual quantitative amounts. In the preferred embodiments, however, these particular agents are expressly limited in both their numbers and their aliquot amounts; and will be not less than one and not more than three different naturally existing nootropic gamma-aminobutyric acid (GABA) neurotransmitter agonists in any prepared admixture of active ingredients. Also when present, each nootropic gamma-aminobutyric acid (GABA) neurotransmitter agonist will appear in an individual quantity ranging from about 10 mg/L to about 5000 mg/L (weight/volume), or alternatively appear in an individual quantity ranging from about 10 mg/Kg to about 5000 mg/Kg (weight/weight).

In addition, the particular number of individual nootropic gamma-aminobutyric acid (GABA) neurotransmitter agonists present in any blended formulation will be accounted for as a neurotransmitter replenishment balance factor in order that the admixture of all essential active agents mathematically is zero ("0") in value. Thus, the actual number of individual nootropic gamma-aminobutyric acid (GABA) neurotransmitter agonists then present in any blended formulation will be chosen carefully and in advance to implement the Neuromodulary Hypothesis described above and expressed by the formula $$\Delta N = [N_1 + N_2 + N_3 + N_4 + N_5] = 0$$

wherein $N_4$ is the net effect of all the individual gamma-aminobutyric acid (GABA) neurotransmitter agonists which are which are inhibitory/relaxant ($-1, -2, -3 \ldots$) versus those other agents [$N_1 + N_5$] which are excitatory/stimulatory ($+1, +2, +3 \ldots$) in effect.

5. The Naturally Existing Adenosine Neurotransmitter Antagonist(s)

In the present invention, naturally occurring nootropic adenosine antagonists are employed as a very different kind of active ingredient; and these are bioactive naturally occurring substances that mimic or function similarly to the nucleoside adenosine or those particular components of the central nervous system that use the nucleoside adenosine in-vivo.

The adenosine receptor is one member of the adenosine receptor group of G protein-coupled receptors which utilizes the nucleoside adenosine as endogenous ligand. Adenosine receptors are implicated in sleep promotion by inhibiting wake-promoting cholinergic neurons in the basal forebrain.

In the human brain, the nucleoside adenosine slows metabolic activity by a combination of different actions. Presynaptically, it reduces synaptic vesicle release. Adenosine receptor blockade produces changes in neurotransmitters by stimulating adenosine kinase and adenosine deaminase—which remove adenosine and prevent it from binding to its receptor. These changes after the normal flow of other neurotransmitters, which in turn then results in major changes to the functions of the human central nervous system.

On this basis therefore, markedly decreasing the activity of the nucleoside adenosine in the human brain will cause a marked improvement of human mood and attitudes; and such a reduction of functional activity for the nucleoside adenosine will correspondingly induce an increase of observable human cognitive functions. Accordingly, each nootropic adenosine antagonist will provide these increases of cognitive function attributes and capabilities in-vivo.

Consequently, any and all naturally occurring nootropic adenosine antagonists—which are either precursor compounds or are themselves a bioactive molecule—are individually and collectively suitable for use as a fifth essential and critical ingredient in the admixture constituting the blended supplement.

Among the preferred examples of acceptable and suitable naturally occurring nootropic adenosine agonists are: caffeine; theophylline; apaxanthine; theobromide; 8-cyclopentyl-1,3-dimethylxanthine (or CPX, 8-cyclopentyltheophylline); 8-cyclopentyl-1,3-dipropylxanthine (or DPCPX); 8-phenyl-1,3-dipropylxanthine; bamifylline; and rolofylline.

In the expected and intended range of blended formulations, the choices of these bioactive agents are carefully controlled as to number of different nootropic adenosine agonists and their individual quantitative amounts. In the preferred embodiments, these particular agents are expressly limited in both numbers and aliquot amounts; and will be not less than one and not more than three different naturally existing nootropic adenosine agonists in any prepared admixture of active ingredients. Also when present, each nootropic adenosine agonist will appear in an individual quantity ranging from about 10 mg/L to about 100 mg/L (weight/volume), or alternatively appear in an individual quantity ranging from about 10 mg/Kg to about 100 mg/Kg (weight/weight).

In addition, the particular number of individual nootropic adenosine agonists present in any blended formulation will be accounted for as a neurotransmitter replenishment balance factor in order that the admixture of all essential active agents mathematically is zero ("0") in value. Thus, the actual number of individual nootropic adenosine agonists then present in any blended formulation will be chosen carefully and in advance to implement the Neuromodulary Hypothesis described above and expressed by the formula $$\Delta N = [N_1 + N_2 + N_3 + N_4 + N_5] = 0$$

wherein $N_5$ is the net effect of all the individual adenosine agonists which are excitatory/stimulatory ($+1, +2, +3 \ldots$) versus those other agents [$N_2 + N_3 + N_4$] which are inhibitory/relaxant ($-1, -2, -3 \ldots$).

VI. Optionally Present and Non-Essential Ingredients of the Blended Supplement A wide collection and selection of optionally present compounds and compositions are available as non-compulsory additions and inclusions to specific formulations of the blended supplements. In each instance, however, these optionally present materials are voluntary choice additions; and will appear and exist as non-requisite and freely elective choice additions to the minimal blended supplement formulations for the making of a commercially salable product. It is must always be remembered however, that these non-essential compounds and compositions are, individually and collectively, always non-mandatory and noncompulsory; and may be freely employed at will or avoided completely and entirely.

A variety of discretionary additives and nonobligatory ingredients may be freely employed as part of the formulation(s) constituting the orally ingestible blended supplement of the present invention. All of these may be used in the alternative; all are extra and non-compulsory discrete compound and compositions; and all are purely voluntary additions which may either be present or be omitted at will.

Optional Non-Essential Ingredient 1: A Flavoring Agent

In general, any type, kind or source of natural fruit flavoring is preferred and is very desirable for use in the fluid blending of the medicament. In this respect, it is of no importance what the particular flavoring is; or what is the chemical composition of the chosen flavoring; or whether or not the particular flavoring agent is a pure substance or a impure mixture of multiple compounds; or whether or not the chosen flavoring agent includes one or more other entities or extraneous substances in addition to the natural flavor extract.

Similarly, it is of no relevance whether the natural flavoring agent is or is not produced in-house by the manufacturer of the medicament; or is obtained as a commercial product made and sold by others. Neither is it material whether or not the flavoring agent is an extract, or a concentrate, or a distillation; nor whether or not it is in solid or liquid form; nor whether or not it is freshly made, frozen, freeze-dried, evaporated, or condensed. All of these matters are deemed to be matters of commercial cost and/or personal preference. Furthermore, in many use instances, two or more different natural flavoring agents can and should be used in combination for best results.

It will be recognized also that, if and when it appears prudent to use them—one or more artificial flavoring agents can be used in place of a natural flavoring agent. The use of artificial flavoring agents, however, is deemed to be a last resort and the least desirable choice.

The proportional ratio range of all the flavoring agents—regardless of whether only a single agent is employed or multiple agents in combination are used—can vary in proportional ratio range from as little as 0.5% (w/v) to as much as 10% (w/v) of the fluid blending. This 0.5%-10% (w/v) proportional ratio range, however, is merely the broadest range deemed to be useful in preparing the medicament. A more desirable proportional ratio range is from about 2.0% to about 8.5% flavoring agent; and a highly preferred proportional ratio range is from about 3.3% to about 5.75% (w/v) flavoring agent.

Merely to demonstrate the acceptable range and to illustrate the variety of suitable natural flavoring agents, the following representative examples are provided.
  (i) Fruit flavorings such as peach extracts, pineapple syrups, apple pie with "crust" extracts, blueberry extracts, raspberry syrups, lime extracts, black cherry syrups, citric fruit extracts, and the like.
  (ii) Maple syrups and molasses.
  (iii) Mint flavorings such as spearmint and peppermint concentrates.
  (iv) Cream, butter, and cheese flavorings.
  (v) Coffee, tea, and chocolate concentrates.
  (vi) Vegetable, plant and nut extracts, flavorings or oils.
  (vii) Candy flavorings.
  (viii) Liquor extracts and flavorings.
  (ix) Spices and spice extracts, flavorings, or oils.
  (x) Vanilla extracts, honey extracts, vinegar extracts, and rose oil extracts.
  (xi) Astringency controlling flavors.

Optional Non-Essential Ingredient 2: A Sweetener

It is often preferred that one or more sweeteners be used whenever in the formulations of the blended supplement; and a wide range and variety of additional sweeteners are conventionally known and commercially sold today for this purpose.

Thus, in any embodiment of the blended supplement, the proportional ratio range of sweetener may vary from as little as about 1.0% (w/v) to as much as about 30% (w/v) of the formulated blending. This 1.0%-30% (w/v) proportional ratio range, however, is merely the broadest range deemed to be useful in preparing the medicament. A more desirable proportional ratio range is from about 2% to about 20% sweetener; and a highly preferred proportional ratio range is from about 5% to about 12% (w/v) sweetener.

Merely illustrating the better-known natural sweeteners commonly available today are the following representative examples: honey; erythritol; sweeteners derived from the Stevia plant; rice syrup; sorghum syrup; sucanat; fructose; agave nectar; barley malt; date sugar; and corn syrup.

Optional Non-Essential Ingredient 3: Minerals

Minerals by broad general definition are used for nutrition; are considered to be necessary in limited quantities in the human diet; and as such, are intended to be consumed daily in at least the minimal recommended doses set forth in the medical and scientific literature. The conventionally recognized common minerals include mineral oxides and polyoxides; and constitute electrolytes and trace elements of the formulation as a whole.

A modest listing of suitable minerals as optional ingredients includes at least the following: calcium, phosphate, iodine, iron, magnesium, and zinc. Other minerals which are typically present in very small amounts for health and metabolism are: electrolytes such as sodium, chloride, potassium; trace elements; prosthetic minerals such fluorine, copper, manganese, cobalt, molybdenum, selenium and chromium; and extremely low concentrations of metals such as nickel, silicon, vanadium, and tin.

Optional Non-Essential Ingredient 4: Starches and Other Forms of Complex Carbohydrates By conventional definition, starch is a polyose found in all assimilating (green) plants. Typically, it is a white hygroscopic powder that can be hydrolysed to dextrin, which in turn is subsequently to hydrolysed d-glucose. Alternatively, enzymatic digestion of starch with the enzyme Diatase will yield maltose.

Optional Non-Essential Ingredient 5: Cellulose-Like Biopolymers

The chemical class of cellulose-like biopolymers includes polysaccharides and oligosaccharides; and is exemplified and represented by Chitosan, chitooligosaccharide, chitin, glucosamine, and other similar complex sugars. Typifying such substances is Chitosan, a cellulose-like biopolymer complex comprised of 6-carbon monosaccharides, whose overall size and molecular weight can vary greatly.

VII. Preferred Formula Requirements and Limitations Of the Blended Supplement The preferred embodiments of the prepared blended formulations are unusually limited in their formulations, and thus are restricted as to:

(i) The ratio proportions of all the individual nootropic neurotransmitter agonists in comparison to all the individual nootropic adenosine antagonists;

(ii) The minimal weight to volume (mg/L) ratio proportions, or alternatively the weight to weight (mg/Kg) ratio proportions, for all the individual neurotransmitter agonists in comparison to all individual adenosine antagonists; and (iii) The neurotransmitter replenishment balance factor for the admixture of essential active agents, which mathematically must be calculated to be zero ("0") in value in every instance.

The Singular Ratio Proportion Limitations

In general, the broad parameters for the admixture of essential bioactive ingredients and their proportional limitations are as follows:

(a) Not less than two and not more than six different naturally existing nootropic dopamine neurotransmitter agonists which are present in a total quantity ranging from about 100 mg/L to about 6000 mg/L, (b) Not less than one and not more than four different naturally existing nootropic acetylecholine neurotransmitter agonists which are present in a total quantity ranging from about 250 mg/L to about 2500 mg/L, (c) At least one and not more than three naturally existing nootropic serotonin neurotransmitter agonists which are present in a total quantity ranging from about 10 mg/L to about 1600 mg/L, (d) At least one and not more than three naturally existing gamma-aminobutyric acid (GABA) neurotransmitter agonists which are present in a total quantity ranging from about 10 mg/L to about 5000 mg/L, and (e) At least one and not more than three nootropic adenosine antagonists which are present in a total quantity ranging from about 10 mg/L to about 100 mg/L, wherein the ratio of all individual nootropic neurotransmitter agonists to all individual nootropic adenosine antagonists is proportionally not less than 7:1 and not more than 16:3, and wherein the minimal weight to volume (mg/L) ratio for all individual neurotransmitter agonists to all individual adenosine antagonists is proportionally not less than about 30:1, and wherein the neurotransmitter replenishment balance factor for the admixture of essential active agents mathematically is zero ("0") in value.

It is critical to understand and appreciate also that, although more than sixty neurotransmitter systems are currently known to exist in the human body, five and only five naturally occurring neurotransmitter systems (designated as N1, N2, N3, N4, and N5 respectively) are employed by the present invention to produce a balanced neuromodulation of the affective neural centers of the brain. In particular, no other neurotransmitter agonistic or antagonistic agents of any kind, functional capacity, chemical composition, or stereochemical structure can be added nor should be included in the blended formulation as an essential active ingredient at any time, for any purpose. According, there is always a complete absence and lack of any other nootropic neurotransmitter agonist(s) or antagonist(s) except for the requisite five classes of active ingredient agents, which are overtly limited to: at least one dopamine agonist, a neural stimulant; at least one acetylcholine agonist, a neural inhibitor; at least one serotonin agonist, a neural inhibitor; at least one GABA agonist, a neural inhibitor; and at least one adenosine antagonist, a neural stimulant.

VIII. Blending Formats for and Physical States of the Supplement

Alternative formulations of an orally ingestable blended supplement can be prepared as a dry powder admixture of active ingredients; or in a liquid carrier format, or as a semi-solid hydrogel; and even in solid suppository form.

Dry Powder Admixtures

Dry admixtures of the five different essential bioactive ingredients can be prepared at will, with or without inclusion of other solid additives. Such dry admixtures will appear in conventionally known formats such as tablets, solid caplets, and hollow gelatin capsules.

In such dry formats, the prepared admixture of active ingredients will exist in powdered or pulverized form and be prepared as either a tablet, or caplet, or as a filled gelatin capsule—which can be swallowed every 6-8 hours by the person in accordance with his individual needs; and such a dry powder admixture format will provide an orally ingestable, efficacious total daily dosage over every 24 hours.

The manufacture of tablets or capsules containing the appropriate admixture dosage is conventionally known and is a common mode of pharmaceutical preparation. Thus, the combination of dry admixture of active ingredients with a variety of inert or quiescent biocompatible substances such as corn starch, sweeteners, flavoring agents, minerals, acid buffering agents, and blending agents will yield a range of different tablets and solid caplets, and gelatin-filled capsules.

Liquid Carriers

The essential purpose and function of a liquid medium or suspension fluid is to serve as a biocompatible carrier for at least the five minimal bioactive and essential ingredients which must be part of every formulation and embodiment of the orally ingestible blended supplement. Thus, the physical state of the resulting fluid supplement can be alternatively a water soluble blending, or be a water miscible blending, or be a blended aqueous suspension as such. Accordingly, any aqueous based fluid which is demonstrably non-reactive, non-toxic, and effectively biochemically neutral in its in-vivo effects is generally suitable for use when preparing the blended supplement.

In addition, because the formulated supplement is to be orally consumed by the person, the blending need not be prepared in sterile form; and it can be prepared in advance of use either in bulk form or as single or multiple dose aliquots; and can typically be stored indefinitely until needed by the individual person.

It is most desirable that the fluid carrier of the blended supplement be biocompatible with the living cells and tissues forming the gastro-intestinal tract and the digestive system of the human body. Thus physiological strength electrolytes are typically present in the carrier fluid; and fluids such as physiological (0.85%-0.90%) saline and 5% sugar solutions are typically employed as carrier media.

In addition, a broad range of other chemical agents and additives may be included in small quantities as optional and non-essential ingredients in alternative formulations of the fluid carrier. Merely illustrating such optional and non-essential ingredients are various minerals, one or more coloring agents, water soluble natural preservatives, and the like.

Semi-Solid Hydrogels

A hydrogel is a colloidal gel in which water is the primary dispersion medium. The retention of color, particle identity, and actives are provided to the hydrogels through the proper selection and combination of functional polymer, colorant, active ingredient, other functional additives, and processing conditions. Proper selection and combination of the components and processing conditions allow stable semi-solid hydrogels to be formed.

In general, hydrogels do not need to be irradiated with ionization energy for the cross-linking effect to be achieved. Suitable functional polymers include alginate, gelatin, gluten, starch, agar, xanthan gum, gellan gum, pectin, guar gum, hydroxypropyl methylcellulose (HPMC), methyl cellulose, microcrystalline cellulose, soy protein, whey protein, casein, collagen, hydrolyzed gelatin, and the like. The more preferred materials are gelatin, gluten, instant starch, and sodium alginate.

Typically, the amount of functional polymer used in the preparation of the hydrogel, before the uptake of water, is from about 1 to about 60 weight percent of the material to be extruded. Preferably the amount of the functional polymer ranges from about 7 to about 50 weight percent. The polymer used frequently has a molecular weight of less than 250,000 daltons, and desirably has a molecular weight of less than 40,000 daltons.

Suppositories

Suppositories are water-in-oil emulsions, but exist primarily as solid dosage forms of a medicament intended for administration within an externally exposed body cavity (such as the rectum or vagina). Suppositories are useful solid drug delivery systems in those situations where it is deemed to be difficult or ineffective to deliver medicine orally; and such an alternate route of effective administration then becomes necessary and appropriate.

Suppositories are formulated using a mixture of different hydrocarbons (such as petrolatum, mineral oils, fatty acids, triglycerides, fats and lipids) to form a biocompatible solid carrier base; and are compounded such that the shaped solid mass will melt, soften, or dissolve within the body cavity where the temperature is around 98.6 degrees F., thereby releasing the active ingredients contained therein.

Suppository carrier base formulations are stable, nonirritating, chemically neutral, and physiologically inert; and typically utilize a variety of different oily or fatty materials (such as cocoa butter, coconut oil, palm kernel oil, and palm oil) which melt or deform at room temperature. Biocompatible carrier base formulations frequently also contain various alcohols, surfactants, emulsifiers, and other blending agents as additives.

IX. Illustrative and Exemplary Formulations

The present invention is a non-prescription blended formulation suitable for oral ingestion by a living human subject, and which after ingestion is able to induce a more positive mood for and to initiate an observable enhancement of cognitive functions in a living human subject.

The intended range and full variety of the blended formulations can and will take alternative formats. As merely illustrative and exemplary of these variants, a minimalist formula, an intermediate formulation, a maximum formula, and a highly preferred blended formulation of essential active ingredients is provided below.

It is critical to understand and appreciate also that, although more than sixty neurotransmitter systems are currently known to exist in the human body, five and only five naturally occurring neurotransmitter systems (designated as N1, N2, N3, N4, and N5 respectively) are employed by the present invention to produce a balanced neuromodulation of the affective neural centers of the brain. In particular, no other neurotransmitter agonistic or antagonistic agents of any kind, functional capacity, chemical composition, or stereochemical structure can be added nor should be included in the blended formulation as an essential active ingredient at any time, for any purpose. According, there is always a complete absence and lack of any other nootropic neurotransmitter agonist(s) or antagonist(s) except for the requisite five classes of active ingredient agents, which are overtly limited to: at least one dopamine agonist, a neural stimulant; at least one acetylcholine agonist, a neural inhibitor; at least one serotonin agonist, a neural inhibitor; at least one GABA agonist, a neural inhibitor; and at least one adenosine antagonist, a neural stimulant.

A Minimalist Formulation

A minimalist blended formulation is a controlled admixture of five types of essential active ingredients, each of which is able to cross the blood-brain barrier in-vivo, wherein the controlled admixture of essential active ingredients is limited to the following:

(i) only two naturally existing nootropic dopamine neurotransmitter agonists, each of which is present in a quantity ranging from about 0.01 g/L to 3.0 g/L, (ii) only one naturally existing nootropic acetylecholine neurotransmitter agonists, each of which is present in a quantity ranging from about 0.01 g/L to 1.5 g/L, (iii) only one naturally existing nootropic serotonin neurotransmitter agonist present in a quantity ranging from about 0.01 g/L to 1.6 g/L, (iv) only one naturally existing gamma-aminobutyric acid neurotransmitter agonist present in a quantity ranging from about 0.01 g/L to 5.0 g/L, (v) only one naturally existing nootropic adenosine antagonist present in a quantity ranging from about 0.01 g/L to 1.0 g/L.

Note also that the "neurotransmitter replenishment balance" of this minimalist admixture mathematically is [+2−1−1−1+1]=0 and properly conforms to the Neuromodulary Hypothesis expressed by the formula $$\Delta N = [N_1 + N_2 + N_3 + N_4 + N_5] = 0$$

An Intermediate Formulation

A intermediate blended formulation is also a controlled admixture of five different types of essential active ingredients, each of which is able to cross the blood-brain barrier in-vivo, wherein the controlled admixture of essential active ingredients is limited to the following:

(a) four different naturally existing nootropic dopamine neurotransmitter agonists which are present in a total quantity ranging from about 400 mg/L to about 2,4000 mg/L, (b) two different naturally existing nootropic acetylecholine neurotransmitter agonists which are present in a total quantity ranging from about 500 mg/L to about 5,000 mg/L, (c) two different naturally existing nootropic serotonin neurotransmitter agonists which are present in a total quantity ranging from about 20 mg/L to about 3,200 mg/L, (d) two different naturally existing nootropic gamma-aminobutyric acid (GABA) neurotransmitter agonists which are present in a total quantity ranging from about 20 mg/L to about 10,000 mg/L, and (e) two different naturally existing nootropic adenosine antagonists which are present in a total quantity ranging from about 20 mg/L to about 200 mg/L.

Note also that the "neurotransmitter replenishment balance" of this intermediate admixture mathematically is [+4−2−2−2+2]=0.

Accordingly, the intermediate blended formulation properly conforms to the Neuromodulary Hypothesis expressed by the formula $$\Delta N = [N_1 + N_2 + N_3 + N_4 + N_5] = 0$$

A Maximum Formulation

A maximum blended formulation is also a controlled admixture of five different types of essential active ingredients, each of which is able to cross the blood-brain barrier in-vivo, wherein the controlled admixture of essential active ingredients is limited to the following:

(a) six different naturally existing nootropic dopamine neurotransmitter agonists which are present in a total quantity ranging from about 600 mg/L to about 36,000 mg/L, (b) three different naturally existing nootropic acetylecholine neurotransmitter agonists which are present in a total quantity ranging from about 750 mg/L to about 7,500 mg/L, (c) three different naturally existing nootropic serotonin neurotransmitter agonists which are present in a total quantity ranging from about 30 mg/L to about 4,800 mg/L, (d) three different naturally existing nootropic gamma-aminobutyric acid (GABA) neurotransmitter agonists which are present in a total quantity ranging from about 30 mg/L to about 15,000 mg/L, and (e) three different naturally existing nootropic adenosine antagonists which are present in a total quantity ranging from about 30 mg/L to about 300 mg/L Note also that the "neurotransmitter replenishment balance" of this intermediate admixture mathematically is [+6−3−3−3+3]=0.

Accordingly, the intermediate blended formulation properly conforms to the Neuromodulary Hypothesis expressed by the formula $$\Delta N = [N_1 + N_2 + N_3 + N_4 + N_5] = 0.$$

A Preferred Formulation

One preferred formulation and the present best embodiment of the blended supplement is a fluid preparation which employs a blend of eight individual nootropic bioactive agents in an isotonic beverage containing about 7% carbohydrate per liter. This preferred formulation contains the following essential bioactive ingredients.

| Compound Name | Quantity Range (mg/L) | [Type Of Active Agent] |
|---|---|---|
| L-Phenylalanine | (100-3000 mg/L) | [a $1^{st}$ dopamine agonist] |
| Phenylethylamine hydrochloride | (100-500 mg/L) | [a $2^{nd}$ dopamine agonist] |
| *Mucuna pruriens* | (50-2500 mg/L) | [a $3^{rd}$ dopamine agonist] |
| Dimethylaminoethanol bitartrate | (100-1500 mg/L) | [a 1st acetylcholine agonist] |
| Pantothenic acid | (10-1000 mg/L) | [a $2^{nd}$ acetylcholine agonist] |
| S-Adenosyl-methionine tosylate disulfate | (100-1600 mg/L) | [a single serotonin agonist] |
| L-Theanine | (100-600 mg/L) | [a single GABA agonist] |
| Caffeine, anhydrous | (20-600 mg/L) | [a single adenosine antagonist] |

Noteably, in this highly preferred formulation:

(i) There are three different dopamine agonists in the blending.

(ii) The minimal total weight quantity of dopamine agonists (3 different agents) present per liter is 110 mg, and the maximum total weight quantity of dopamine agonists (3 different agents) present per liter is 6000 mg.

(iii) There are two different acetylcholine agonists in the blending.

(iv) The minimal total weight quantity of acetylcholine agonists (2 different agents) present per liter is 250 mg, and the maximum total weight quantity of acetylcholine agonists (2 different agents) present per liter is 2500 mg.

(v) There is only a single serotonin agonist in the blending.

(vi) L-Theanine is the sole GABA agonist in the blending.

(vii) There is only a single adenosine antagonist in the blending.

(viii) The type number ratio of the five requisite types of active agents in the blending—i.e., the proportions of individual dopamine agonist/acetylcholine agonist/serotonin agonist/GABA agonist/adenosine antagonist—is 3:2:1:1:1.

(ix) The minimal weight-to-volume ratio for the five types of requisite active agents in the blending is 5.0:2.2:2.0:2.0:0.4.

(x) The maximum weight-to-volume ratio for the five types of requisite active agents in the blending is 10.0:4.2:3.2:1.0:1.0.

(xi) The neurotransmitter replenishment balance factor for the blending as a whole mathematically is zero in value, and properly conforms to the Neuromodulary Hypothesis expressed by the formula $$\Delta N = [N_1 + N_2 + N_3 + N_4 + N_5] = 0.$$

X. The In-Vivo Method of Treatment

The Methodology as a Whole

The present invention provides a method for initiating an improvement of human mood and inducing an observable enhancement of cognitive functions in a living human subject. This method comprises the following steps:

Step 1: obtaining an orally ingestable non-prescription blended supplement comprising a limited admixture of essential bioactive agents as described previously wherein (i) the ratio of all individual nootropic neurotransmitter agonists to all individual nootropic adenosine antagonists is proportionally not less than 7:1 and not more than 16:3; and (ii) the minimal weight to volume (mg/L) ratio for all individual neurotransmitter agonists to all individual adenosine antagonists is proportionally not less than about 30:1, and (iii) the neurotransmitter replenishment balance for the admixture of essential active agents mathematically is zero ("0") in value, and properly conforms to the Neuromodulary Hypothesis expressed by the formula $$\Delta N = [N_1 + N_2 + N_3 + N_4 + N_5] = 0.$$

Step 2: Orally administering said blended supplement to a living human subject in a predetermined quantity sufficient to initiate an improvement of human mood and induce an observable enhancement of cognitive functions in a living human subject.

Step 3: Allowing at least a minimal time period after ingestion for said orally administered quantity of blended supplement to become assimilated by and to act within the body of said living human subject. An average time period for assimilation is 5-40 minutes; and most typically is less than 30 minutes.

Step 4: Periodically monitoring the human subject for objective indications of a positive mental state and an observable enhancement of cognitive functions. Qualitative assessment scores of 0 to 10 (10 being very positive feeling of well being) have been reported by test candidates in empiric studies following an oral intake of the prepared blended formulation as a ingested beverage of 3 drinks during a 48 hour period.

Step 5: Determining from said objective indications that a more positive mental state exists and an observable enhancement of cognitive functions has occurred in the living human subject. Qualitative assessments tested the prepared blended formulation as a ingested beverage in 200 subjects and the average resulting score was between 8.0 and 8.5 (10 being very positive feeling of well being).

Range of Expected Dosages & Frequency of Administrations

The primary and most preferred mode of administration for the blended supplement is by simple oral ingestion. To initiate a more favorable state of mind and to induce an enhancement of cognitive functions, an effective amount or aliquot for oral intake will vary from about 50 mg (the minimal effective concentration) to not more than 6000 mg (the maximal effective concentration) per day. A highly preferred effective concentration for oral ingestion will range from about 600 mg to about 3,000 mg over 24 hours time.

In addition, although the effective oral dosage of blended supplement can be taken by the person as a single daily administration, it is far more preferable that the total daily dosage of blended supplement be ingested only in part on any given occasion; and that preferably, a series of 2-5 individual oral administrations of far smaller doses at fixed time intervals be made over each 24 hour time period. In this manner, a more uniform level of bioactive agents are introduced and present within the human body at any given time; and a more consistent efficacious effect is maintained over each 24 hour treatment cycle.

For liquids, about 120-150 ml of blended formulation constitutes a single dose amount. As a prepared beverage, the 120-150 ml of blended formulation will contain about 2.5 grams of the five essential neuroactive agents (excluding sugars, flavorings, etc.). A 3 drink limit over a 24 hour period of time is suggested.

Duration of Induced Effects

The expected duration of induced effects after orally ingesting the blended supplement is expected to be variable among susceptible individuals, ranging from 2 or 3 hours to as long as 8 hours, with a half life of about 4 hours in typical human subjects. The test subject will typically feel effects in less than 30 minutes; and these effects will last from about 2 to about 8 hours, with an average half life of 4 hours. In general therefore, this means that after 4 hours duration, there should be about a 50% reduction in the observed neuroactive effects for the person.

Precautions, Contradictions And Side Effects

No side effects at all were encountered by the 200 human test subjects tested. As to possible contraindications, it is advised that the following individuals do not consume this any form of these blended formulations: Pregnant or nursing women; children less than 13 years old; persons who are phenylketonurics; anyone taking MAO inhibitors for depression; anyone with uncontrolled hypertension and/or cardiac condition, unless cleared by their doctor. No drug interactions as such are presently known.

XI. In-Vivo Experiments and Resulting Empirical Data

To demonstrate the merits and value of the present invention, a variety of experimental human case studies and resulting empirical data are presented below. It will be expressly understood, however, that the facts and data provided below are merely the best evidence of the subject matter as a whole which is the present invention; and that these human case studies are only illustrative of the full scope of the present invention as envisioned and claimed.

A set of clinical trials were performed using the median dosing of a 'typical formulation' in randomly selected normal, healthy volunteers ranging from 14 to 80 years (mean age 44.5 years) greater than 50 kg body weight over a 10 day period. At the end of the clinical trial, subjects were asked to subjectively rate the feeling of mood enhancement, ranging from a scale of 0 (no change) to 10 (euphoric) and to rate the duration of effect (in hours) following ingestion of the prepared beverage. Members also were encouraged to report any side effects, if any.

Test Groupings

Eight different test groups of ten human subjects each (N=10) were devised as follows:

Test Group 1: Oral solution containing 125 mL juice (7% carbohydrate), 3 times daily. This formulation represents placebo.

Test Group 2: L-Phenylalanine, 800 mg and mucina pruriens, 15% L-DOPA, 200 mg oral solution in 125 mL juice (containing 7% carbohydrate), 3 times daily. This nootropic formulation affects the following neurotransmitter systems: dopamine agonist, a stimulant. The type number ratio is 2:0:0:0:0 to produce a $\Delta N = +2$. This agent fails the test for producing predictable mood enhancement because it is has an imbalanced type number ratio, resulting in a net stimulatory effect ($\Delta N = +2$), and producing a predictable mood over stimulation.

Test Group 3: Phenylethylamine hydrochloride, 400 mg oral solution in 125 mL juice (containing 7% carbohydrate), single dose. This nootropic formulation affects the following neurotransmitter systems: dopamine agonist, a stimulant. The type number ratio is 1:0:0:0:0 to produce a $\Delta N = +1$. This agent fails the test for producing predictable mood enhancement because it is has an imbalanced type number ratio, resulting in a net stimulatory effect ($\Delta N = +1$), and producing a predictable mood over stimulation.

Test Group 4: Dimethylaminoethanol bitartrate, 300 mg oral solution in 125 mL juice (containing 7% carbohydrate), 3 times daily. This nootropic formulation affects the following neurotransmitter systems: acetylcholine agonist, an inhibitor. The type number ratio is 0:1:0:0:0 to produce a $\Delta N=-1$. This agent fails the test for producing predictable mood enhancement because it is has an imbalanced type number ratio, resulting in a net inhibitory effect ($\Delta N=-1$), and producing a predictable mood suppression.

Test Group 5: S-Adenosyl-methionine tosylate disulfate, 300 mg oral solution in 125 mL juice (containing 7% carbohydrate), 3 times daily. This nootropic formulation affects the following neurotransmitter systems: serotonin agonist, an inhibitor. The type number ratio is 0:0:1:0:0 to produce a $\Delta N=-1$. This agent fails the test for producing predictable mood enhancement because it is has an imbalanced type number ratio, resulting in a net inhibitory effect ($\Delta N=-1$), and producing a predictable mood suppression.

Test Group 6: Anhydrous caffeine, 80 mg oral solution in 125 mL juice (containing 7% carbohydrate), 3 times daily. This nootropic formulation affects the following neurotransmitter systems: adenosine antagonist, a stimulant. The type number ratio is 0:0:0:0:1 to produce a $\Delta N=+1$. This agent fails the test for producing predictable mood enhancement because it is has an imbalanced type number ratio, resulting in a net stimulatory effect ($\Delta N=+1$), and producing a predictable mood over stimulation.

Test Group 7: L-Theanine, 200 mg oral solution in 125 mL juice (containing 7% carbohydrate), 3 times daily. This nootropic formulation affects the following neurotransmitter systems: GABA agonist, an inhibitor. The type number ratio is 0:0:0:1:0 to produce a $\Delta N=-1$. This agent fails the test for producing predictable mood enhancement because it is has an imbalanced type number ratio, resulting in a net inhibitory effect ($\Delta N=-1$), and producing a predictable mood suppression.

Test Group 8: Single doses of L-phenylalanine (500 mg), phenylethylamine hydrochloride (400 mg), mucuna pruriens, 15% L-DOPA (200 mg), dimethylaminoethanol bitartrate (200 mg), S-adenosyl-methionine tosylate disulfate (200 mg), L-theanine (200 mg), and caffeine (80 mg) oral solution in 125 mL juice (containing 7% carbohydrate). This nootropic formulation affects the following neurotransmitter systems: dopamine agonist, a stimulant; acetylcholine agonist, an inhibitor; serotonin agonist, an inhibitor; GABA agonist, an inhibitor; and adenosine antagonist, a stimulant. The type number ratio is 3:2:1:1:1 to produce a $\Delta N=+3-2-1-1+1=0$. The net physiologic result is optimal balanced mood enhancement Empirical Results The results in each group are summarized below:
Test Group 1—Score 1.0; marginal effect, lasting about 15 minutes. No side effects reported.
Test Group 2—Score 4.0; somewhat happy, lasting about 1 to 2 hours. Side effects of anxiety and tremors in 3 of 10 subjects.
Test Group 3—Score 7.5; temporary euphoric feeling lasting less than 30 minutes. Side effects of flushing in 4 of 10 subjects.
Test Group 4—Score 2.0; mild effect, lasting less than 1 hour. Side effects of headache in 1 of 10 subjects.
Test Group 5—Score of 6.0; better mood, lasting 3 hours. No side effects reported.
Test Group 6—Score of 3.0; felt alert, lasting 2 hours. No side effects reported.
Test Group 7—Score of 6.5; very calm, sedative-like effect, lasting 3 hours. No side effects reported.
Test Group 8—Score of 8.5; euphoric feeling lasting about 30 minutes, followed by a nice aura for about 4 hours. No side effects reported.

Results and Conclusions

The results of these preliminary clinical trials present a clinically significant positive mood enhancement in those human test subjects which received a combination of different bioactive agents, in low dose amounts, and which produce a balanced nootropic neurotransmitter effect when directly compared to placebo subjects (Test Group 1) and individuals receiving less than all five types of bioactive agents (Test Groups 2 through 7 respectively).

In addition, with few exceptions, doses of individual constituents produced a marginal effect when using three times the dosing quantity when compared to the formulation received by Test Group 8 [Single doses of L-phenylalanine (500 mg), phenylethylamine hydrochloride (400 mg), mucuna pruriens, 15% L-DOPA (200 mg), dimethylaminoethanol bitartrate (200 mg), S-adenosyl-methionine tosylate disulfate (200 mg), L-theanine (200 mg), and caffeine (80 mg) as an oral solution in 125 mL juice (containing 7% carbohydrate)].

The most significant and meaningful clinical effects were seen in test groups receiving: Phenylethyamine hydrochloride as an active agent, which produced a noticeable but short-term effect of less than 30 minutes; and S-adenosyl-methionine tosylate disulfate as an active agent, which produced moderate mood enhancement but also required 4 to 5 times the dosing.

All of the active agents employs as formula constituents have a good safety profile, which allows for a large and varied dosing range. Also, toxicity is exceedingly low for the formulated dose limits. Such side effects as were reported by a very few test subjects were mild and self-limited, and included only flushing, tremors, anxiety, and headache. The highly preferred formulation of the blended supplement as a specifically prepared beverage has been tested in over 200 human volunteers, without any reported side effects.

The present invention is neither restricted in form nor limited in scope except by the claims appended hereto.

What we claim is:
1. A non-prescription blended formulation suitable for ingestion by a living human subject, comprising: (a) two or more different naturally existing nootropic dopamine neurotransmitter agonists, (b) one or more naturally existing nootropic acetylcholine neurotransmitter agonists, (c) one or more naturally existing nootropic serotonin neurotransmitter agonists, (d) one or more naturally existing nootropic gamma-aminobutyric acid (GABA) neurotransmitter agonists, and (e) one or more nootropic adenosine antagonists, wherein the ratio of all individual nootropic neurotransmitter agonists to all individual nootropic adenosine antagonists is proportionally not less than 5:1, wherein the neurotransmitter replenishment balance for the admixture of essential active agents mathematically is zero ("0") in value; and wherein there is a complete absence of any other kind of nootropic agonist or antagonist.
2. The blended formulation of claim 1, wherein each of said different nootropic neurotransmitter agonists is one selected from the group consisting of precursor compositions and synapse active molecules.

3. The blended formulation of claim 2, further comprising a biocompatible and non-toxic carrier medium selected from the group consisting of aqueous liquids and semi-solid hydrogels.

4. The blended formulation of claim 1, wherein each individual nootropic dopamine neurotransmitter agonist is selected from the group consisting of L-phenylalanine, L-tyrosine, N-acetyl-L-tyrosine, L-3,4-dihydroxyphenylalanine (L-DOPA), phenylethylamine, biopterin, amineptine, methylphenidate, selegiline, rasagiline, ropinirole, pramipexole, mucuna pruriens, modafinil, and citicoline.

5. The blended formulation of claim 1, wherein each individual nootropic acetylcholine neurotransmitter agonist is selected from the group consisting of choline, 2-dimethylaminoethanol (DMAE), meclofenoxate, alpha-glycerylphosphorylcholine (alpha-GPC), acetylcarnitine, pantothenic acid (Vitamin $B_5$), galantamine, huperzine A, donepezil, ispronicline, nicotine, and arecoline.

6. The blended formulation of claim 1, wherein each nootropic serotonin neurotransmitter agonist is selected from the group consisting of 5-hydroxytryptophan (or 5-HTP, 5-hydroxy-L-tryptophan), pyridoxal phosphate, pyridoxal-5'-phosphate, mesembrine, resveratrol, curcumin, piperine, harmal, rhodiola rosea, and tianeptine.

7. The blended formulation of claim 1, wherein each individual nootropic GABA neurotransmitter agonist is selected from the group consisting of ethanol, picrotoxin, and L-theanine.

8. The blended formulation of claim 1, wherein each individual nootropic adenosine receptor antagonist is selected from the group consisting of caffeine, theophylline, apaxanthine, theobromide, 8-cyclopentyl-1,3-dimethylxanthine (or CPX, 8-cyclopentyltheophylline), 8-cyclopentyl-1,3-dipropylxanthine (or DPCPX), 8-phenyl-1,3-dipropylxanthine, bamifylline, and rolofylline.

9. A fluid, non-prescription, blended formulation suitable for oral ingestion by a living human subject, comprising: (i) at least two and not more than six different naturally existing nootropic dopamine neurotransmitter agonists, (ii) at least one and not more than four different naturally existing nootropic acetylcholine neurotransmitter agonists, (iii) at least one and not more than three different naturally existing nootropic serotonin neurotransmitter agonists, (iv) at least one and not more than three different naturally existing nootropic GABA neurotransmitter agonists, (v) at least one and not more than three different naturally existing nootropic adenosine antagonists, and a biocompatible and non-toxic liquid carrier medium, wherein the ratio of all individual nootropic neurotransmitter agonists to all individual nootropic adenosine antagonists is proportionally not less than 5:1 and not more than 16:3, wherein the neurotransmitter replenishment balance for the admixture of essential active agents mathematically is zero ("0") in value, and wherein there is a complete absence of any other kind of nootropic agonist or antagonist.

10. The blended formulation of claim 9, wherein each of said different nootropic neurotransmitter agonists is one selected from the group consisting of precursor compositions and synapse active molecules.

11. The blended formulation of claim 10, wherein said biocompatible and non-toxic carrier medium is one selected from the group consisting of aqueous liquids and semi-solid hydrogels.

12. The blended formulation of claim 9, wherein each individual nootropic dopamine neurotransmitter agonist is selected from the group consisting of L-phenylalanine, L-tyrosine, N-acetyl-L-tyrosine, L-DOPA, phenylethylamine, biopterin, amineptine, methylphenidate, selegiline, rasagiline, ropinirole, pramipexole, mucuna pruriens, modafinil, and citicoline.

13. The blended formulation of claim 9, wherein each individual nootropic acetylcholine neurotransmitter agonist is selected from the group consisting of choline, DMAE, meclofenoxate, alpha-GPC, acetylcarnitine, Vitamin $B_5$, galantamine, huperzine A, donepezil, ispronicline, nicotine, and arecoline.

14. The blended formulation of claim 9, wherein each individual nootropic serotonin neurotransmitter agonist is selected from the group consisting of 5-hydroxytryptophan (or 5-HTP, 5-hydroxy-L-tryptophan), pyridoxal phosphate, pyridoxal-5'-phosphate, mesembrine, resveratrol, curcumin, piperine, harmal, rhodiola rosea, and tianeptine.

15. The blended formulation of claim 9, wherein each individual nootropic gamma-aminobutyric acid neurotransmitter agonist is selected from the group consisting of ethanol, picrotoxin, and L-theanine.

16. The blended formulation of claim 9, wherein each individual nootropic adenosine receptor antagonist is selected from the group consisting of caffeine, theophylline, apaxanthine, theobromide, 8-cyclopentyl-1,3-dimethylxanthine (or CPX, 8-cyclopentyltheophylline), 8-cyclopentyl-1,3-dipropylxanthine (or DPCPX), 8-phenyl-1,3-dipropylxanthine, bamifylline, and rolofylline.

* * * * *

UNITED STATES PATENT AND TRADEMARK OFFICE
CERTIFICATE OF CORRECTION

| | |
|---|---|
| PATENT NO. | : 8,609,162 B2 |
| APPLICATION NO. | : 13/689980 |
| DATED | : December 17, 2013 |
| INVENTOR(S) | : Vincent Giuliano et al. |

It is certified that error appears in the above-identified patent and that said Letters Patent is hereby corrected as shown below:

On the Title Page, Item (56), under "Other Publications", in column 2, line 1, delete "CEREBREX" and insert -- CELEBREX --, therefor.

On the Title Page, Item (56), under "Other Publications", in column 2, line 14, delete "CerebralHealth,com" and insert -- CerebralHealth.com --, therefor.

On Title Page 2, Item (56), under "Other Publications", in column 2, line 13, delete "at" and insert -- et --, therefor.

In the Specification

In column 2, line 35, delete "acetycholine." and insert -- acetylcholine. --, therefor.

In column 4, line 7, delete "coreuleus," and insert -- coeruleus, --, therefor.

In column 4, line 10, delete "substania" and insert -- substantia --, therefor.

In column 5, line 32, delete "addiction" and insert -- addiction. --, therefor.

In column 9, line 7, delete "device" and insert -- device. --, therefor.

In column 10, line 2, delete "serotinin," and insert -- serotonin, --, therefor.

In column 13, line 24, delete "Recetams" and insert -- Racetams --, therefor.

In column 14, line 5, delete "Racetarns." and insert -- Racetams. --, therefor.

In column 14, line 13, delete "Racetarns" and insert -- Racetams --, therefor.

In column 15, line 5, delete "Gingko" and insert -- Ginkgo --, therefor.

In column 15, line 21, delete "disnct" and insert -- distinct --, therefor.

In column 15, line 23, delete "cecarboxylase." and insert -- decarboxylase. --, therefor.

In column 16, line 4, delete "depreny" and insert -- deprenyl); --, therefor.

In column 16, line 13, delete "Serotonoin" and insert -- Serotonin --, therefor.

In column 16, lines 61-62, delete "acetylecholine" and insert -- acetylcholine --, therefor.

Signed and Sealed this
Sixth Day of May, 2014

Michelle K. Lee
*Deputy Director of the United States Patent and Trademark Office*

In column 17, line 28, delete "acetylecholine" and insert -- acetylcholine --, therefor.

In column 19, line 44, delete "nucleaus" and insert -- nucleus --, therefor.

In column 24, line 24, delete "stochiometric" and insert -- stoichiometric --, therefor.

In column 24, line 53, delete "stochiometric quanitites" and insert -- stoichiometric quantities --, therefor.

In column 25, line 12, delete "Iv." and insert -- IV. --, therefor.

In column 25, line 22, delete "acetylecholine" and insert -- acetylcholine --, therefor.

In column 26, line 50, delete "Acetycholine" and insert -- Acetylcholine --, therefor.

In column 30, line 24, delete "apaxanthine;" and insert -- paraxanthine; --, therefor.

In column 32, line 55, delete "Diatase" and insert -- Diastase --, therefor.

In column 33, line 29, delete "acetylecholine" and insert -- acetylcholine --, therefor.

In column 36, line 35, delete "acetylecholine" and insert -- acetylcholine --, therefor.

In column 36, lines 65-66, delete "acetylecholine" and insert -- acetylcholine --, therefor.

In column 37, lines 30-31, delete "acetylecholine" and insert -- acetylcholine --, therefor.

In column 40, line 49, delete "mucina" and insert -- mucuna --, therefor.

In column 42, line 29, delete "Phenylethyamine" and insert -- Phenylethylamine --, therefor.